United States Patent [19]
Stemp et al.

[11] Patent Number: 6,080,752
[45] Date of Patent: Jun. 27, 2000

[54] TRICYCLIC AMINE DERIVATIVES

[75] Inventors: Geoffrey Stemp; Stephen Allan Smith, both of Bishop's Stortford; Christopher Norbert Johnson, Saffron Waldon; Phillip Jeffrey, Datchworth, all of United Kingdom

[73] Assignee: SmithKline Beecham PLC, Brentford, United Kingdom

[21] Appl. No.: 09/202,335

[22] PCT Filed: Jun. 6, 1997

[86] PCT No.: PCT/EP97/02985

§ 371 Date: Dec. 14, 1998

§ 102(e) Date: Dec. 14, 1998

[87] PCT Pub. No.: WO97/47602

PCT Pub. Date: Dec. 18, 1997

[30] Foreign Application Priority Data

Jun. 11, 1996 [GB] United Kingdom .................. 9612153

[51] Int. Cl.[7] ...................... A61K 31/473; A61K 31/404; C07D 221/10; C07D 209/60; C07D 265/36
[52] U.S. Cl. ...................... 514/290; 514/229.8; 514/291; 514/411; 544/101; 546/89; 546/101; 548/427; 548/430
[58] Field of Search ...................... 546/101, 89; 544/101; 548/427, 430; 514/290, 291, 229.8, 411

[56] References Cited

U.S. PATENT DOCUMENTS 5,318,966  6/1994  Bruderer .............................. 514/232.8

FOREIGN PATENT DOCUMENTS

| 0 126 486 | 9/1983 | European Pat. Off. . |
| 0 127 597 | 4/1984 | European Pat. Off. . |
| 0 410 535 | 7/1990 | European Pat. Off. . |
| 0 548 664 | 12/1992 | European Pat. Off. . |
| 2 729 145 | 12/1996 | European Pat. Off. . |
| WO91/00856 | 1/1991 | WIPO . |
| WO92/20655 | 11/1992 | WIPO . |
| WO92/21654 | 12/1992 | WIPO . |
| WO95/14006 | 5/1995 | WIPO . |
| WO97/17326 | 5/1997 | WIPO . |

OTHER PUBLICATIONS

Sonesson, et al., Substituted (s)–Phenylpiperidines and Rigid Congeners as Preferential Dopamine Autoreceptor Antagonists: Synthesis and Structure–Activity Relationships, J Med. Chem., vol. 37, pp. 2734–2753 (1994).

Lin, et al, Centrally Acting Serotonergic and Dopaminergic agents. 1. Synthesis and Structure–Activity Relationships of 2,3,3a, 4,5,9b–Hexahydro–1H–benz[e]indole Derivatives, J. Med. Chem. vol. 36, pp. 1053–1068 (1993).

*Primary Examiner*—Evelyn Mei Huang
*Attorney, Agent, or Firm*—Soma G. Simon; William T. King; Charles M. Kinzig

[57] ABSTRACT

A compound of formula (I):

Formula (I)

wherein $R^1$ represents a group of formula (A) or (B):

(A)

(B)

$R^2$, $R^3$, Ar, Y Ar$^1$ are as defined herein; or a pharmaceutically acceptable salt thereof, which has activity at dopamine receptor and is useful in the treatment of psychoses

9 Claims, No Drawings

TRICYCLIC AMINE DERIVATIVES

This application is the national phase of PCT/EP97/02985, Jun. 6, 1997.

The present invention relates to novel tricyclic amine derivatives, processes for their preparation, pharmaceutical compositions containing them and their use in therapy, as modulators of dopamine $D_3$ receptors, in particular as antipsychotic agents.

We have now found a class of tricyclic amine derivatives which have affinity for dopamine receptors, in particular the $D_3$ receptor, and thus potential in the treatment of conditions wherein modulation of the $D_3$ receptor is beneficial, e.g. as antipsychotic agents.

In a first aspect the present invention provides compounds of formula (I):

Formula (I)

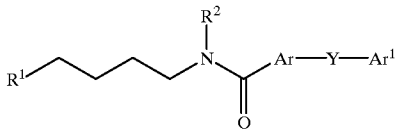

wherein $R^1$ represents a group of formula (A) or (B):

(A)

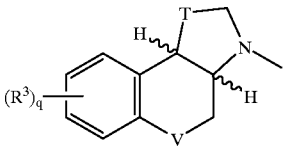

(B)

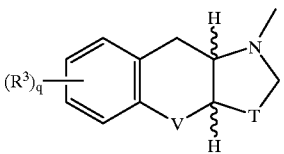

$R^2$ represents a hydrogen atom or a $C_{1-4}$alkyl group;

$R^3$ represents a substituent selected from: a hydrogen or halogen atom, a hydroxy, cyano, trifluoromethyl, trifluoromethoxy, trifluoromethanesulfonyloxy, $C_{1-4}$alkyl, $C_{1-4}$alkoxy, aryl$C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl, $C_{1-4}$alkylsulphonyl, $C_{1-4}$alkylsulphonyloxy, $C_{1-4}$alkylsulphonyl$C_{1-4}$alkyl, arylsulphonyl, arylsulphonyloxy or arylsulphonyl$C_{1-4}$alkyl group, a group $R^{3'}OCO(CH_2)_p$, $R^{3'}R^4NCO(CH_2)_p$ or $R^{3'}R^4NSO_2(CH_2)_p$ where each of $R^{3'}$ and $R^4$ independently represents a hydrogen atom or a $C_{1-4}$alkyl group and p represents zero or an integer from 1 to 4, or a group $Ar^2$—Z, wherein $Ar^2$ represents an optionally substituted phenyl ring or an optionally substituted 5- or 6-membered aromatic heterocyclic ring and Z represents a bond, O, S, or $CH_2$;

q is 1 or 2;

T represents $CH_2$, $CH_2CH_2$ or $OCH_2$;

V represents $CH_2$, O or a bond;

Ar and $Ar_1$ each independently represent an optionally substituted phenyl ring or an optionally substituted 5- or 6-membered aromatic heterocyclic ring; and Y represents a bond, —NHCO—, —CONH—, —$CH_2$—, or —$(CH_2)_mY^1(CH_2)_n$—, wherein $y^1$ represents O, S, $SO_2$, or CO and m and n each represent zero or 1 such that the sum of m+n is zero or 1;

and salts thereof.

In the compounds of formula (I) above an alkyl group or moiety may be straight or branched. Alkyl groups which may be employed include methyl, ethyl, n-propyl, n-butyl, n-pentyl, n-hexyl and any branched isomers thereof such as isopropyl, t-butyl, sec-pentyl, and the like.

When $R^3$ represents an aryl$C_{1-4}$alkoxy, arylsulphonyl, arylsulphonyloxy or arylsulphonyl$C_{1-4}$alkyl group, the aryl moiety may be selected from an optionally substituted phenyl ring or an optionally substituted 5- or 6-membered heterocyclic ring.

A halogen atom present in the compounds of formula (I) may be fluorine, chlorine, bromine or iodine.

When q is 2, the substituents $R^3$ may be the same or different. Preferably q represents 1.

When Ar, $Ar^1$ or $Ar^2$ represents an optionally substituted phenyl group this may carry one or more substituents selected from: a hydrogen or halogen atom, or a hydroxy, cyano, nitro, $C_{1-4}$alkyl, $C_{1-4}$alkoxy $C_{1-4}$alkanoyl or $C_{1-4}$alkylsulphonyl group.

An optionally substituted 5- or 6-membered heterocyclic aromatic ring, as defined for either of the groups Ar, $Ar^1$ or $Ar^2$ may contain from 1 to 4 heteroatoms selected from O, N or S. When the ring contains 2–4 heteroatoms, one is preferably selected from O, N and S and the remaining heteroatoms are preferably N. Examples of 5 and 6-membered heterocyclic groups include furyl, thienyl, pyrrolyl, oxazolyl, thiazolyl, imidazolyl, oxadiazolyl, thiadiazolyl, pyridyl, triazolyl, triazinyl, pyridazyl, pyrimidinyl and pyrazolyl. The heterocyclic ring may be optionally substituted by one or more substituents selected from: a hydrogen or halogen atom, or a hydroxy, cyano, nitro, $C_{1-4}$alkyl, $C_{1-4}$alkoxy $C_{1-4}$alkanoyl or $C_{1-4}$alkylsulphonyl group.

It will be appreciated that for use in medicine the salts of formula (I) should be physiologically acceptable. Suitable physiologically acceptable salts will be apparent to those skilled in the art and include for example acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulphonic, methanesulphonic or naphthalenesulphonic acid. Other non-physiologically acceptable salts e.g. oxalates, may be used, for example in the isolation of compounds of formula (I) and are included within the scope of this invention. Also included within the scope of the invention are solvates and hydrates of compounds of formula (I).

It will be appreciated that the compounds of formula (I) contain two or more asymmetric centres. Such compounds can exist in diastereomeric forms, namely cis and trans isomers; both forms and all mixtures thereof are included within the scope of this invention. Furthermore, each diastereoisomer can exist as optical isomers (enantiomers). Both the pure enantiomers, racemic mixtures (50% of each enantiomer) and unequal mixtures of the two are included within the scope of the invention. In accordance with convention the (+) and (−) designations used herein indicate the direction of rotation of plane-polarised light by the compounds. The prefix (+) indicates that the isomer is dextrorotatory (which can also be designated d) and the prefix (−) indicates the levorotatory isomer (which can also be designated l). It will thus be appreciated that the invention extends to the individual diastereoisomers, individual enantiomers and any and all mixtures of these forms.

Particular compounds according to the invention include:

trans-7-methoxy-4-(4-(4-phenylbenzoylamino)butyl)-1,2,3,4,4a,5,6,10b-octahydrobenzo[f]quinoline;
cis-7-methoxy-4-(4-(4-phenylbenzoylamino)butyl)-1,2,3,4,4a,5,6,10b-octahydrobenzo[f]quinoline;
trans-7-hydroxy-4-(4-(4-phenylbenzoylamino)butyl)-1,2,3,4,4a,5,6,10b-octahydrobenzo[f]quinoline;
cis-7-hydroxy-4-(4-(4-phenylbenzoylamino)butyl)-1,2,3,4,4a,5,6,10b-octahydrobenzo[f]quinoline;
trans-7-methylsulfonyloxy-4-(4-(4-phenylbenzoylamino)butyl)-1,2,3,4,4a,5,6,10b-octahydrobenzo[f]quinoline;
cis-7-methylsulfonyloxy-4-(4-(4-phenylbenzoylamino)butyl)-1,2,3,4,4a,5,6,10b-octahydrobenzo[f]quinoline;
trans-4-(4-(4-phenylbenzoylamino)butyl)-1,2,3,4,4a,5,6,10b-octahydrobenzo[f]quinoline;
cis-4-(4-(4-phenylbenzoylamino)butyl)-1,2,3,4,4a,5,6,10b-octahydrobenzo[f]quinoline;
cis-2,3,3a,4,9,9a-hexahydro-1-(4-(4-phenylbenzoylamino)butyl)-1H-benz[f]indole;
cis-2,3,3a,4,9,9a-hexahydro-5-methoxy-1-(4-(4-phenylbenzoylamino)butyl)-1H-benz[f]indole;
trans-8-methoxy-4-(4-(4-phenylbenzoylamino)butyl)-1,2,3,4,4a,5,6,10b-octahydrobenzo[f]quinoline;
trans-2,3,3a,4,5,9b-hexahydro-3-(4-(4-phenylbenzoylamino)butyl)-1H-benz[e]indole;
trans-2,3,3a,4,5,9b-hexahydro-6-methoxy-3-(4-(4-phenylbenzoylamino)butyl-1H-benz[e]indole;
(4aS, 10bS)-trans-7-methoxy-4-(4-(4-phenylbenzoylamino)butyl)-1,2,3,4,4a,5,6,10b-octahydrobenzo[f]quinoline;
trans-8-hydroxy-4-(4-(4-phenylbenzoylamino)butyl)-1,2,3,4,4a,5,6,10b-octahydrobenzo[f]quinoline;
trans-2,3,3a,4,5,9b-hexahydro-6-hydroxy-3-(4-(4-phenylbenzoylamino)butyl)-1H-benz[e]indole;
(4aS, 10bS)-trans-7-hydroxy-4-(4-(4-phenylbenzoylamino)butyl)-1,2,3,4,4a,5,6,10b-octahydrobenzo[f]quinoline;
trans-2,3,3a,4,5,9b-hexahydro-6-methylsulfonyloxy-3-(4-(4-phenylbenzoylamino)butyl)-1H-benz[e]indole;
(4aS, 10bS)-trans-7-methylsulfonyloxy-4-(4-(4-phenylbenzoylamino)butyl)-1,2,3,4,4a, 5,6,10b-octahydrobenzo[f]quinoline;

and salts thereof.

The present invention also provides a process for preparing compounds of formula (I) which process comprises:

(a) reacting a compound of formula (II):

$R^1H$            Formula (II)

wherein $R^1$ is as hereinbefore defined;

with a compound of formula (III):

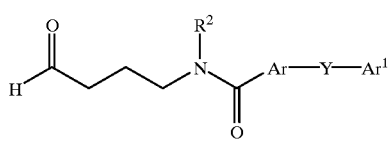

Formula (III)

wherein $R^2$, Y, Ar and $Ar^1$ are as hereinbefore defined;

(b) reaction of a compound of formula (IV):

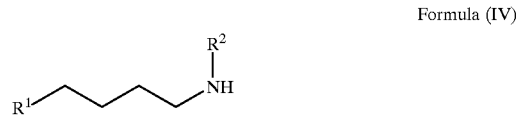

Formula (IV)

wherein $R^1$ and $R^2$ are as hereinbefore defined;
with a compound of formula (V):

$Ar^1—Y—ArCOX$        Formula (V)

wherein Y, Ar and $Ar^1$ are as hereinbefore defined and X is a halogen atom or the residue of an activated ester;

(c) to prepare a compound of formula (I) where Y is a bond, reaction of a compound of formula (VI):

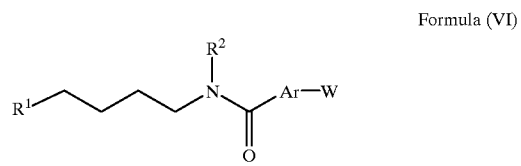

Formula (VI)

wherein $R^1$, $R^2$ and Ar are as hereinbefore defined, and W is a halogen atom or a trifluoromethylsulphonyloxy group, or W is a group M selected from a boron derivative e.g. a boronic acid function $B(OH)_2$ or a metal function such as trialkylstannyl e.g. $SnBu_3$, zinc halide or magnesium halide;
with a compound:

$Ar^1—W^1$ wherein $W^1$ is a halogen atom or a trifluoromethylsulphonyloxy group when W is a group M, or $W^1$ is a group M when W is a halogen atom or a trifluoromethylsulphonyloxy group.

(d) interconversion of one compound of formula (I) to a different compound of formula (I) e.g. (i) alkylation of a compound (I) wherein $R^2$ represents hydrogen, (ii) conversion of one $R^3$ from alkoxy (e.g.methoxy) to hydroxy, or (iii) conversion of $R^3$ from hydroxy to sulphonyloxy, e.g. alkylsulphonyloxy or trifluoromethanesulphonyloxy; (iv) conversion of a compound wherein Y represents S to a compound wherein Y is $SO_2$ or (v) conversion of Y from CO to $CH_2$; and optionally thereafter forming a salt of formula (I).

Process (a) requires the presence of a reducing agent. Suitable reducing agents which may be employed include sodium borohydride, cyanoborohydride or triacetoxyborohydride under acidic conditions, or catalytic hydrogenation. The reaction may conveniently be effected in a solvent such as ethanol. The compound of formula (II) may be employed in this process as a mixture of cis and trans isomers, but more preferably the cis and trans isomers are separated prior to reaction with a compound (III). When $R^1$ represents a group of formula (A) and T represents $CH_2CH_2$ the compound of formula (II) is advantageously employed as the trans isomer.

Process (b) may be effected by methods well known in the art for formation of an amide bond.

Reaction of a compound of formula (VI) with $Ar^1W^1$, according to process (c) may be effected in the presence of a transition metal e.g. palladium catalyst such as bis-triphenylphosphinepalladium dichloride or tetrakis-triphenylphosphinepalladium (0). When M represents a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. The substituent W is preferably a halogen atom such as bromine, or a sulphonyloxy group such as trifluoromethylsulphonyloxy; and $W^1$ is preferably a goup M, such as trialkylstannyl or $B(OH)_2$.

Interconversion reactions according to process (d) may be effected using methods well known in the art.

Compounds of formula (II) wherein $R^1$ represents a group of formula (A) and T represents $CH_2CH_2$ may be prepared for example according to the following reaction scheme (I) (see also Cannon, J. G.; et al., J. Med. Chem., 1976 (19) 987–993):

(ii) product of (b)(i) reacted with a methylating agent such as iodomethane in a solvent such as dimethoxyethane in the presence of a base such as sodium hydride.

(c)
(i) reduction of the oxo function, using a reducing agent such as sodium bis-(2-methoxyethoxy) aluminium hydride in toluene (Red-Al).
(ii) reduction of the double bond using a reducing agent such as sodium borohydride in a solvent such as methanol. This step results in a mixture of cis and trans isomers, which may be separated at this stage, or following demethylation.

(d) demethylation using standard methods e.g. reaction with 1-chloroethylchloroformate.

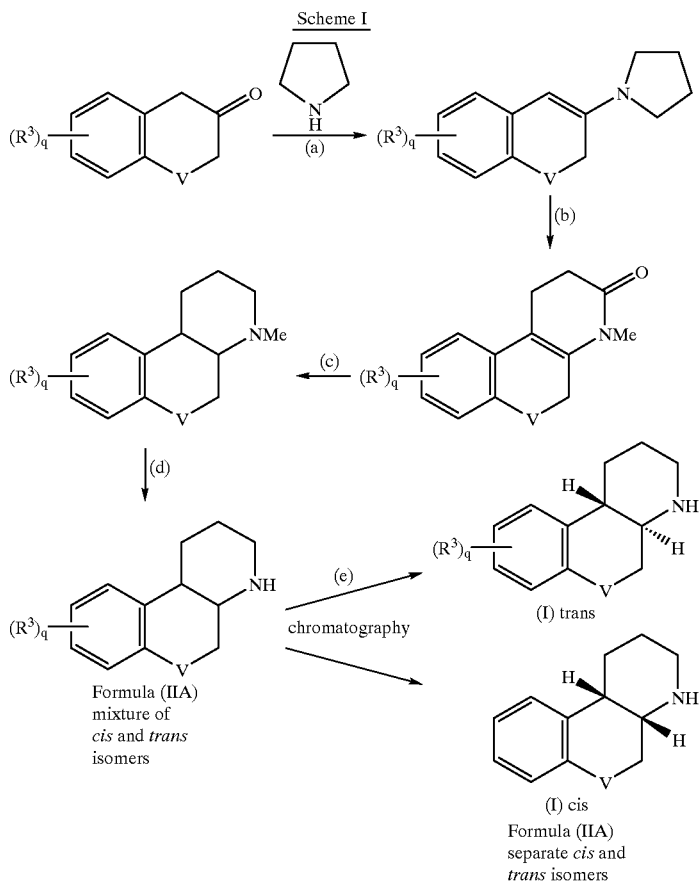

Reaction conditions
(a) solvent such as benzene, under reflux conditions with p-toluenesulphonic acid in catalytic quantity;
(b)
(i) cyclisation, e.g. by heating with acrylamide at elevated temperature (>50° C.).

(e) separation of cis and trans isomers by conventional methods e.g. chromatography.

Alternatively compounds of formula (II) wherein $R^1$ is a group (A) and T is $CH_2CH_2$ may be obtained as the trans isomers according to the following reaction scheme (II):

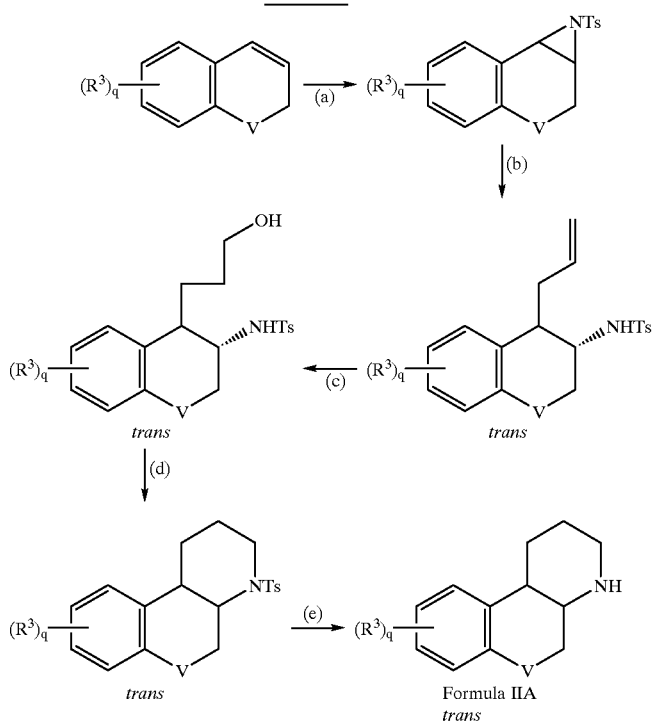

Reaction Conditions (a) formation of aziridine ring e.g. using PhI=NTs in the presence of a copper catalyst such as Cu(II) acetylacetonate (Cu(acac)$_2$) or Cu(II)triflate (Cu(OTF)$_2$). Alternatively a chiral catalyst may be employed (see D. A. Evans et al., J. Am. Chem. Soc., 1993, 115, 5328 and E. N. Jacobsen et al., J. Am. Chem. Soc., 1993, 115, 5326). The single enantiomers of the aziridines produced by the methodology described in the above references can be converted to the corresponding enantiomers of the amines of Formula (IIA) by the process described in Scheme II.

(b) ring opening using a Grignard reagent, e.g. allyl magnesium bromide in a solvent such as diethyl ether.

(c)
  (i) hydroboration of the double bond using e.g. borane in a solvent such as tetrahydrofuran, followed by oxidation, using e.g. hydrogen peroxide.

(d)
  (i) conversion of the hydroxy function to a leaving group using e.g. methanesulphonyl chloride or p-toluenesulphonyl chloride, followed by
  (ii) cyclisation under basic conditions (e.g. potassium carbonate).

(e) cleavage of the N-tosyl group by reductive methods e.g. using lithium aluminium hydride, or Red-Al.

When R1 is a group (B) and T represents CH$_2$, compounds of formula (II) may be prepared by the procedure described by C-H Lin et al., J. Med. Chem., 1993, 36, 1069–1083, according to Scheme (III):

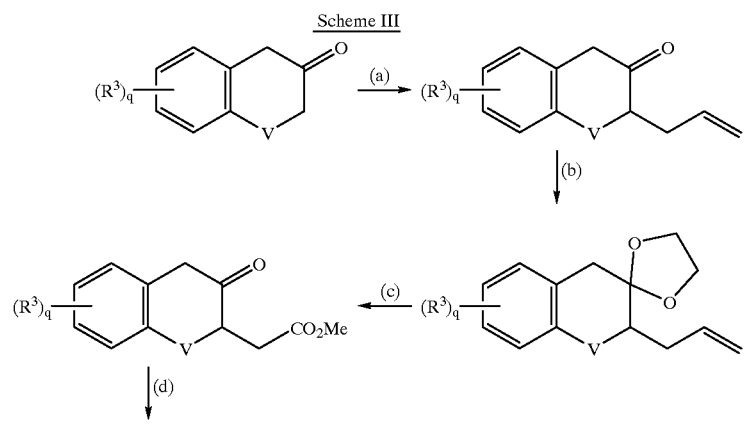

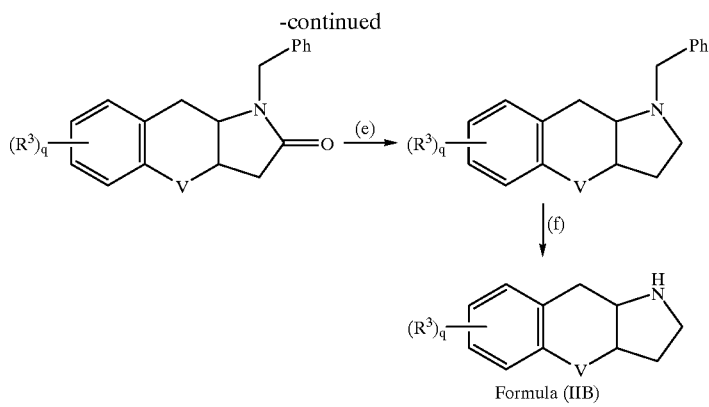

Formula (IIB)

Reaction Conditions
(a) Insertion of 2-propenyl function by the following steps:
   (i) Lithium diisopropylamide, (MeO)$_2$CO, tetrahydrofuran;
   (ii) Lithium diisopropylamide, allyl bromide, tetrahydrofuran;
   (iii) Lithium chloride in dimethylsulphoxide or sodium chloride in dimethylformamide.
(b) formation of ketal by reaction with trimethyl orthoformate, ethanediol and p-toluenesulphonic acid in dichloromethane,
(c) oxidative cleavage of double bond with formation of carboxylate function followed by acetal cleavage by reaction with
   (i) potassium permanganate and sodium periodate in water,
   (ii) acetonitrile and methanolic hydrochloric acid.
(d) cyclisation by reaction with amine under reductive conditions e.g. benzylamine, acetic acid, sodium cyanoborohydride.
(e) reduction of oxo function using e.g. lithium aluminium hydride in tetrahydrofuran.
(f) cleavage of N-protecting group (benzyl) by standard methods e.g. catalytic hydrogenation using e.g. palladium hydroxide or by reaction with 1-chloroethylchloroformate.

Compounds of formula (III) are known or may be prepared using standard procedures.

A compound of formula (IV) may be prepared by alkylation of a compound (II) by standard methods. Thus, for example a compound of formula (II) may be reacted with N-(4-bromobutylphthalimide) followed by removal of the phthalimide group to give a compound of formula (IV) where R$^2$ is hydrogen. Compounds where R$^2$ is alkyl may be prepared by subsequent reaction with the appropriate aldehyde using conditions analogous to process (a) above.

Compounds of formula (VI) may be prepared by processes analogous to (a) or (b) described above. Compounds Ar$^1$W$^1$ are commercially available or may be prepared by standard methods.

It will be appreciated that compounds of formula (IV) or formula (VI) may be prepared as in the form of cis or trans isomers, or mixtures thereof, starting with the appropriate isomer of formula (II).

Compounds of formula (I) have been found to exhibit affinity for dopamine receptors, in particular the D$_3$ receptor, and are expected to be useful in the treatment of disease states which require modulation of such receptors, such as psychotic conditions. Compounds of formula (I) have also been found to have greater affinity for dopamine D$_3$ than for D$_2$ receptors. The therapeutic effect of currently available antipsychotic agents (neuroleptics) is generally believed to be exerted via blockade of D$_2$ receptors; however this mechanism is also thought to be responsible for undesirable extrapyramidal side effects (eps) associated with many neuroleptic agents. Without wishing to be bound by theory, it has been suggested that blockade of the recently characterised dopamine D$_3$ receptor may give rise to beneficial antipsychotic activity without significant eps. (see for example Sokoloff et al, Nature, 1990; 347: 146–151; and Schwartz et al, Clinical Neuropharmacology, Vol 16, No. 4, 295–314, 1993). Preferred compounds of the present invention are therefore those which have higher affinity for dopamine D$_3$ than dopamine D$_2$ receptors (such affinity can be measured using standard methodology for example using cloned dopamine receptors). Said compounds may advantageously be used as selective modulators of D$_3$ receptors.

We have found that certain compounds of formula (I) are dopamine D$_3$ receptor antagonists, others may be agonists or partial agonists. The functional activity of compounds of the invention (i.e. whether they are antagonists, agonists or partial agonists) can be readily determined using the test method described hereinafter, which does not require undue experimentation. D$_3$ antagonists are of potential use as antipsychotic agents for example in the treatment of schizophrenia, schizo-affective disorders, psychotic depression and mania. Conditions which may be treated by dopamine D$_3$ receptor agonists include dyskinetic disorders such as Parkinson's disease, neuroleptic-induced parkinsonism and tardive dyskinesias; depression; anxiety, memory disorders, sexual dysfunction and drug (e.g. cocaine) dependency.

In a further aspect therefore the present invention provides a method of treating conditions which require modulation of dopamine D$_3$ receptors, for example psychoses such as schizophrenia, which comprises administering to a subject in need thereof an effective amount of a compound of formula (I) or a physiologically acceptable salt thereof.

The invention also provides the use of a compound of formula (I) or a physiologically acceptable salt thereof in the manufacture of a medicament for the treatment of conditions which require modulation of dopamine D$_3$ receptors, for example psychoses such as schizophrenia.

A preferred use for D$_3$ antagonists according to the present invention is in the treatment of psychoses such as schizophrenia.

A preferred use for D$_3$ agonists according to the present invention is in the treatment of dyskinetic disorders such as Parkinson's disease.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg,e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

Biological Test Methods

The ability of the compounds to bind selectively to human $D_3$ dopamine receptors can be demonstrated by measuring their binding to cloned receptors. The inhibition constants ($K_i$) of test compounds for displacement of $[^{125}I]$ iodosulpride binding to human $D_3$ dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at $-40°$ C. Crude cell membranes were prepared by homogenisation followed by high-speed centrifugation, and characterisation of cloned receptors achieved by radioligand binding.

Preparation of CHO Cell Membranes

Cell pellets were gently thawed at room temperature, and resuspended in about 20 volumes of ice-cold 50 mM Tris salts (pH 7.4 @ 37° C.), 20mM EDTA, 0.2 M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4 @ 37° C.), using an Ultra-Turrax, and recentrifuged at 18,000 r.p.m for 15 min at 4° C. in a Sorvall RC5C. The membranes were washed two more times with ice-cold 50 mM Tris salts (pH 7.4 @ 37° C.). The final pellet was resuspended in 50 mM Tris salts (pH 7.4 @ 37° C.), and the protein content determined using bovine serum albumin as a standard (Bradford, M. M. (1976) Anal. Biochem. 72, 248–254).

Binding Experiments on Cloned Dopamine Receptors

Crude cell membranes were incubated with 0.1 nM $[^{125}I]$ iodosulpride (~2000 Ci/mmol; Amersham, U. K.), and the test compound in a buffer containing 50 mM Tris salts (pH 7.4 @ 37° C.), 120 mM NaCl, 5 mM KCl, 2 mM $CaCl_2$, 1 mM $MgCl_2$, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4 @ 37° C.), 120 mM NaCl, 5 mM KCl, 2 mM $CaCl_2$, 1 mM $MgCl_2$. The radioactivity on the filters was measured using a Cobra gamma counter (Canberra Packard). Non-specific binding was defined as the radioligand binding remaining after incubation in the presence of 100 μM iodosulpride. For competition curves, 14 concentrations (half-log dilutions) of competing cold drug were used.

Competition curves were analysed simultaneously whenever possible using non-linear least-squares fitting procedures, capable of fitting one, two or three site models.

Compounds of Examples tested according to this method had pKi values in the range 6.5–9.0 at the human dopamine $D_3$ receptor.

Functional Activity at Cloned Dopamine Receptors

The functional activity of compounds at human D2 and human D3 receptors (ie agonism or antagonism) may be determined using a Cytosensor Microphysiometer (McConnell HM. et. al., Science, 1992, 257, 1906–1912). In Microphysiometer experiments, cells (hD2_CHO or hD3_CHO) were seeded into 12 mm Transwell inserts (Costar) at 300000 cells/cup in foetal calf serum (FCS)-containing medium. The cells were incubated for 6 h at 37° C. in 5% $CO_2$, before changing to FCS-free medium. After a further 16–18 h, cups were loaded into the sensor chambers of the Cytosensor Microphysiometer (Molecular Devices) and the chambers perfused with running medium (bicarbonate-free Dulbecco's modified Eagles medium containing 2 mM glutamine and 44 mM NaCl) at a flow rate of 100 ul/min. Each pump cycle lasted 90s. The pump was on for the first 60s and the acidification rate determined between 68 and 88s, using the Cytosoft programme. Test compounds were diluted in running medium. In experiments to determine agonist activity, cells were exposed (4.5 min for hD2, 7.5 min for hD3) to increasing concentrations of putative agonist at half hour intervals. Seven concentrations of the putative agonist were used. Peak acidification rate to each agonist concentration was determined and concentration-response curves fitted using Robofit [Tilford, N. S., Bowen, W. P. & Baxter, G. S. Br. J. Pharmacol. (1995) in press]. In experiments to determine antagonist potency, cells were treated at 30 min intervals with five pulses of a submaximal concentration of quinpirole (100 nM for hD2 cells, 30 nM for hD3 cells), before exposure to the lowest concentration of putative antagonist. At the end of the next 30 min interval, cells were pulsed again with quinpirole (in the continued presence of the antagonist) before exposure to the next highest antagonist concentration. In all, five concentrations of antagonist were used in each experiment. Peak acidification rate to each agonist concentration was determined and concentration-inhibition curves fitted using Robofit.

Pharmaceutical Formulations

The following represent typical pharmaceutical formulations according to the present invention, which may be prepared using standard methods.

| IV Infusion | |
|---|---|
| Compound of formula (I) | 1–40 mg |
| Buffer | to pH ca 7 |
| Solvent/complexing agent | to 100 ml |
| Bolus Injection | |
| Compound of formula (I) | 1–40 mg |
| Buffer | to pH ca 7 |
| Co-Solvent | to 5 ml |

Buffer
  Suitable buffers include citrate, phosphate, sodium hydroxide/hydrochloric acid.
Solvent
  Typically water but may also include cyclodextrins (1–100 mg) and co-solvents such as propylene glycol, polyethylene glycol and alcohol.

| Tablet | |
|---|---|
| Compound | 1–40 mg |
| Diluent/Filler* | 50–250 mg |
| Binder | 5–25 mg |
| Disentegrant* | 5–50 mg |
| Lubricant | 1–5 mg |
| Cyclodextrin | 1–100 mg |

*may also include cyclodextrins
Diluent: e.g. Microcrystalline cellulose, lactose, starch
Binder: e.g. Polyvinylpyrrolidone, hydroxypropymethylcellulose
Disintegrant: e.g. Sodium starch glycollate, crospovidone
Lubricant: e.g. Magnesium stearate, sodium stearyl fumarate.

| Oral Suspension | |
|---|---|
| Compound | 1–40 mg |
| Suspending Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |

Suspending agent: e.g. Xanthan gum, microcrystalline cellulose
Diluent: e.g. sorbitol solution, typically water
Preservative: e.g. sodium benzoate
Buffer: e.g. citrate
Co-solvent: e.g. alcohol, propylene glycol, polyethylene glycol, cyclodextrin The invention is further illustrated by the following non-limiting examples:

DESCRIPTION 1

1-(5-Methoxy-3,4-dihydronaphthalen-2-yl)-pyrrolidine

A mixture of 5-methoxy-2-tetralone (100 g, 0.68 mmol), pyrrolidine (85.7 ml, 1.03 mol) and p-toluenesulfonic acid (100 mg, catalytic) in benzene (1.2L) was heated at reflux under Dean-Stark conditions for 4 h. The mixture was cooled and the solvent evaporated to give the title compound as a brown oil (155 g, 99%).

Mass spectrum (API$^+$): 230 (MH$^+$, 100%) $C_{15}H_{19}NO$ requires 299.

$^1$H NMR (CDCl$_3$) δ: 1.90 (4H, m), 2.45 (2H, t, J=7 Hz), 2.84 (2H, t, J=7 Hz), 3.28 (4H, m), 3.80 (3H, s), 5.10 (1H, s), 6.48 (1H, d, J=13 Hz), 6.53 (1H, d, J=13 Hz), 7.0 (1H, m, J=7 Hz).

The following compound was prepared in a similar manner to description 1

(a) 1-(6-Methoxy-3,4-dihydronaphthalen-2-yl)-pyrrolidine hu 1H NMR (CDCl$_3$) δ: 1.91 (4H, m), 2.46 (2H, t, J=8 Hz), 2.81 (2H, t, J=8 Hz), 3.24 (4H, m), 3.77 (3H, s), 5.12 (1H, s), 6.63 (2H, m), 6.78 (1H, m).

DESCRIPTION 2

7-Methoxy-1,4,5,6-tetrahydro-2H-benzo[f]quinolin-3-one

A mixture of acrylamide (146 g, 2.0 mol) and 1-(5-methoxy-3,4-dihydronaphthalen-2-yl)pyrrolidine (156 g, 0.68 mol) was heated at 80° C. for 2 h and then 130° C. for a further 0.75 h. The mixture was cooled and water (1L) was added. The resultant brown precipitate was collected by filtration, washed with water and dried in vacuo. Trituration with hot ethanol (2L) gave the title compound as a white solid (35.9 g, 23%).

Mass spectrum (API$^+$): 230 (MH$^+$, 100%) $C_{14}H_{15}NO_2$ requires 229.

$^1$H NMR (CDCl$_3$)δ: 2.35 (2H, bt, J=8Hz), 2.7 (4H, m), 2.92 (2H, t, J=8 Hz), 3.85 (3H, s), 6.75 (2H, m, J=8 Hz), 7.18 (1H, m, J=8 Hz), 7.9 (1H, br s).

The following compound was prepared in a similar manner to description 2

(a) 8-Methoxy-1,4,5,6-tetrahydro-2H-benzo[f]quinolin-3-one $^1$H NMR (CDCl$_3$) δ: 2.37 (2H, t, J=8 Hz), 2.67 (4H, m), 2.99 (2H, t, J=8 Hz), 3.80 (3H, s), 6.74 (2H, m), 7.04 (1H, d, J=9 Hz), 8.00 (1H, br s).

DESCRIPTION 3

7-Methoxy-4-methyl-1,4,5,6-tetrahydro-2H-benzo[f]quinoline-3-one

A mixture of 7-methoxy-1,4,5,6-tetrahydro-2H-benzoquinolin-3-one (20 g, 87 mmol) and sodium hydride (80% dispersion in oil, 2.9 g, 96 mmol) in anhydrous dimethoxyethane (300 ml) was heated at reflux, under argon for 3 h. The mixture was cooled, iodomethane (21.7 ml, 349 mmol) added and the mixture refluxed for a further 4.5 h. The mixture was cooled and water (10 ml) was added dropwise with ice cooling. The resultant mixture was concentrated and the residue partitioned between water (50 ml) and dichloromethane (3×50 ml). The combined organic extracts were dried (Na$_2$SO$_4$) and evaporated in vacuo to give the title compound as a solid (19.6 g, 92%).

Mass spectrum (API$^+$): 244 (MH$^+$, 100%) C$_{15}$H$_{17}$NO$_2$ requires 243.

$^1$H NMR (CDCl$_3$) δ: 2.25 (2H, t, J=8 Hz), 2.43 (4H, s), 2.71 (2H, t, J=8 Hz), 2.95 (3H, s), 3.65 (3H, s), 6.56 (2H, m, J=8 Hz), 6.98 (1H, m, J=8 Hz)

The following compound was prepared in a similar manner to description 3.

(a) 8-Methoxy-4-methyl-1,4,5,6-tetrahydro-2H-benzo[f]quinolin-3-one

Mass spectrum (API$^+$): Found 244 (MH$^+$). C$_{15}$H$_{17}$O$_2$ requires 243.

DESCRIPTION 4

7-Methoxy-4-methyl-1,2,3,4,5,6-hexahydrobenzo[f]quinoline

A solution of sodium bis-(2-methoxyethoxy)aluminium hydride in toluene (Red-Al, 65% wt, 37.2 ml, 124 mmol) was added to a stirred solution of 7-methoxy-4-methyl-1,4,5,6-tetrahydro-2H-benzo[f]quinoline-3-one (10 g, 41.2 mmol) in toluene (200 ml). The mixture was heated at reflux, under argon for 6 h and allowed to cool. Water (7 ml) was added dropwise with ice cooling and the aluminium salts dissolved by addition of 50% KOH (37 ml). The organic phase was separated, washed with water (2×100 ml), dried (Na$_2$SO$_4$) and concentrated in vacuo to afford an oil which was chromatographed on silica gel, with 10–15% ethyl acetate-pentane gradient elution to give the title compound as a yellow oil (5.5 g, 58%)

Mass spectrum (API$^+$): 230 (MH$^+$, 100%) C$_{15}$H$_{19}$NO requires 229.

$^1$H NMR (CDCl$_3$) δ: 2.0 (2H, m), 2.35 (4H, m), 2.62 (3H, s), 2.80 (2H, t, J=8 Hz), 3.05 (2H, t, J=8 Hz), 3.81 (3H, s), 6.60 (1H, d, J=9 Hz), 6.68 (1H, d, J=9 Hz), 7.1 (1H, m, J=8 Hz).

The following compound was prepared in a similar manner to description 4.

(a) 8-Methoxy-4-methyl-1,2,3,4,5,6-hexahydrobenzo[f]quinoline

Mass spectrum (API$^+$): Found 230 (MH$^+$). C$_{15}$H$_{19}$NO requires 229.

DESCRIPTION 5 cis-and trans-7-Methoxy-4-methyl-1,2,3,4,4a,5,6,10b-octahydrobenzo[f]quinoline

Sodium borohydride (1.61 g, 42 mmol) was added portionwise over 5 min to a stirring solution of 7-methoxy-4-methyl-1,2,3,4,5,6-hexahydrobenzo[f]quinoline (5.4 g, 23 mmol) in methanol (400 ml). The mixture was stirred at room temperature under argon for 72 h. Acetic acid (10 ml) was added dropwise and the mixture was concentrated in vacuo. The residue was basified with saturated Na$_2$CO$_3$(50 ml) and extracted into ether (3×30 ml). The combined organic extracts were washed with water, dried (Na$_2$SO$_4$) and the solvent evaporated to give the title compound as a yellow oil (4.5 g, 84%).

Mass spectrum (API$^+$): 232 (MH$^+$, 100%) C$_{15}$H$_{21}$NO requires 231.

$^1$H NMR (CDCl$_3$) δ: 1.45–2.20 (6H, m), 2.30–2.67 (6H, m), 2.80–3.05 (3H, m), 3.80 and 3.82 (3H, 2xs), 6.65–7.13 (3H, m).

The following compound was prepared in a similar manner to description 5.

(a) cis and trans-(±)-8-Methoxy-4-methyl-1,2,3,4,4a,5,6,10b-octahydrobenzo[f]quinoline Mass spectrum (API$^+$): Found 232 (MH$^+$). C$_{15}$H$_{21}$NO requires 231.

DESCRIPTION 6a trans-7-Methoxy-1,2,3,4,4a,5,6,10b-octahydrobenzo[f]quinoline and

DESCRIPTION 6b cis-7-Methoxy-1,2,3,4,4a5,6,10b-octahydrobenzo[f]quinoline 1-Chloroethylchloroformate (4.62 ml, 42.8 mmol) was added with stirring to an ice cooled solution of cis-and trans-7-methoxy-4-methyl-1,2,3,4,4a,5,6,10b-octahydrobenzo[f]quinoline (4.3 g, 18.6 mmol) in dichloromethane (140 ml). The mixture was allowed to warm to room temperature and stirred for a further 2 h. Diisopropylethylamine (4.9 ml, 28 mmol) was added and the mixture heated at reflux for 1 h. The mixture was cooled and concentrated in vacuo before dissolving in methanol (100 ml) and refluxing for 1 h. After cooling, the solvent was removed and the residue partitioned between saturated aqueous K$_2$CO$_3$ (50 ml) and dichloromethane (3×50 ml). The combined organic extracts were washed with brine (50 ml), dried (Na$_2$SO$_4$) and the solvent evaporated to afford a yellow oil. Chromatography on silica using 10% methanol-dichloromethane and 6.6 ml/L 0.880 ammonia as eluent gave trans 7-methoxy-1,2,3,4,4a,5,6,10b-octahydrobenzo[f]quinoline (0.6 g, 30%) as the first eluting isomer.

Mass spectrum (API$^+$): 218 (MH$^+$ 100%) C$_{14}$H$_{19}$NO requires 217.

$^1$H NMR (CDCl$_3$) δ: 1.48–2.25 (7H, m), 2.55–3.0 (5H, m), 3.15–3.25 (1H, m), 3.81 (3H, s), 6.68 (1H, d, J=7 Hz), 6.85 (1H, d, J=7 Hz), 7.15 (1H, t, J=7 Hz).

cis-7-Methoxy-1,2,3,4,4a,5,6,10b-octahydrobenzo(f)quinoline (1 g, 50%) was obtained as the second eluting isomer.

Mass spectrum (API$^+$): 218 (MH$^+$, 100%) C$_{14}$H$_{19}$NO requires 217.

$^1$H NMR (CDCl$_3$) δ: 1.40–1.85 (4H, m), 2.20–2.61 (7H, m), 2.68–2.85 (1H, m), 2.90–3.05 (1H, m), 3.61 (3H, s), 6.5 (1H, d, J=8 Hz), 6.72 (iH, d, J=8 Hz), 6.98 (1H, t, J=8 Hz).

The following compounds were prepared in a similar manner to descriptions 6a and 6b.

(c) (±)-trans-8-Methoxy-1,2,3,4,4a,5,6,10b-octahydrobenzo[f]quinoline (first eluting isomer)

$^1$H NMR (CDCl$_3$) δ: 1.24 (1H, m), 1.60–2.05 (4H, m), 2.50 (2H, m), 2.59–3.00 (5H, m), 3.20 (1H, m), 3.76 (3H, s), 6.62 (1H, d, J=3 Hz), 6.74 (1H, dd, J=9, 3 Hz), 7.18 (1H, d, J=9 Hz).

(d) (±)-cis-8-Methoxy-1,2,3,4,4a,5,6,10b-octahydrobenzo[f]quinoline (second eluting isomer)

$^1$H NMR (CDCl$_3$) δ: 1.63 (2H, m), 1.88 (3H, m), 2.17 (1H, m), 2.92 (5H, m), 3.14 (1H, br s), 3.35 (1H, m), 3.79 (3H, s), 6.62 (1H, d, J=3 Hz), 6.73 (1H, dd, J=9, 3 Hz), 7.09 (1H, d, J=9 Hz).

DESCRIPTION 7 cis-and trans4-Methyl-1,2,3,4,4a,5,6,10b-octahydrobenzo[f]quinoline

Prepared from 2-tetralone using a procedure similar to that of Description 1 to 5 inclusive.

Mass Spectrum (API$^+$): 202 (MH$^+$, 100%) C$_{14}$H$_{19}$N requires 201.

$^1$H NMR (CDCl$_3$) δ: 1.15–2.20 (6H, m), 2.25–3.05 (9H, m), 7.00–7.35 (4H, m).

DESCRIPTION 8a trans-1,2,3,4,4a,5,6,10b-Octahydrobenzo[f]quinoline and

DESCRIPTION 8b cis-1,2,3,4,4a,5,6,10b-Octahydrobenzo[f]quinoline

1-Chloroethylchloroformate (2.01 ml, 18.61 mmol) was added with stirring to an ice-cooled solution of cis-and trans-4-methyl-1,2,3,4,4a,5,6,10b-octahydrobenzo[f]quinoline (1.66 g, 8.34 mmol) in dichloromethane (60 ml). The mixture was allowed to warm to room temperature and stirred for a further 2 h. Diisopropylethylamine (2.2 ml, 12.6 mmol) was added and the mixture heated at reflux for 1 h. The mixture was cooled and concentrated in vacuo, dissolved in methanol and refluxed for 1 h. After cooling, the solvent was removed and the residue partitioned between saturated aqueous K$_2$CO$_2$ and dichloromethane (4×50 ml). The combined organic extracts were washed with water, dried (Na$_2$SO$_4$) and the solvent evaporated to afford an oil. Chromatography on silica using 10% methanol-ethyl acetate with 6.6 ml/L 0.880 ammonia as eluent gave the trans-isomer of the title compound (260 mg, 33%) as the first eluting product.

Mass spectrum (API$^+$) 188 (100%, MH$^+$) C$_{13}$H$_{17}$N requires 187.

$^1$H NMR (CDCl$_3$) δ: 1.31 (1H, m), 1.83 (4H, m), 2.03 (1H, m), 2.55 (2H, m), 2.75 (2H, m), 2.94 (1H, m), 3.25 (1H, m), 4.3 (1H, br s), 7.00–7.35 (4H, m).

The cis-isomer of the title compound (170 mg, 21 %) was obtained as the second eluting product.

Mass spectrum (API$^+$): 188 (MH$^+$, 100%). C$_{13}$H$_{17}$N requires 187.

$^1$H NMR (CDCl$_3$) δ: 1.54 (2H, m), 1.76 (1H, m), 1.84 (1H, m), 1.97 (1H, m), 2.16 (1H, m), 2.43 (1H, br s), 2.83 (2H, m), 2.9 (2H, m), 2.93 (1H, m), 3.26 (1H, m), 7.00–7.25 (4H, m).

DESCRIPTION 9

3,4-Dihydro-2-hydroxynaphthalenecarboxylic Acid, Methyl Ester

To a stirred solution of 2-tetralone (25.0 g, 171 mmol) in dry tetrahydrofuran (250 ml) at 0° C. under argon was added lithium diisopropylamide (111 ml, 2M solution, 222 mmol). After stirring at 0° C. for 1 h, dimethyl carbonate was added (145 ml, 1710 mmol). After stirring at 0° C. for 0.5 h, the reaction mixture was warmed to room temperature, and then heated at reflux for 16 h. The mixture was then cooled to 0° C. and quenched with hydrochloric acid (1M, 450 ml). The resulting mixture was extracted with ethyl acetate (3×1000 ml) and the combined extracts were washed with brine (1000 ml) then dried (Na$_2$SO$_4$) and evaporated in vacuo to afford the title compound as a dark brown oil (36.3 g, 100%).

Mass spectrum (API$^-$): 203 (M—H)$^-$ C$_{12}$H$_{12}$O$_3$ requires 204.

$^1$H NMR (CDCl$_3$) δ: 2.54 (2H, t, J=8 Hz), 2.83 (2H, t, J=8 Hz), 3.92 (3H, s), 7.03–7.30 (3H, m), 7.70 (1H, d, J=9 Hz), 13.32 (1H, s).

DESCRIPTION 10

3,4-Dihydro-2-hydroxy-3-(2-propenyl)-naphthalenecarboxylic Acid, Methyl Ester

To a stirred solution of 3,4-dihydro-2-hydroxynaphthalene carboxylic acid, methyl ester (36.2 g, 177 mmol) in dry tetrahydrofuran (440 ml) at −30° C. under argon was added dropwise lithium diisopropylamide (195 ml, 2M solution, 390 mmol). Allyl bromide (24.3 ml, 284 mmol) was then added at 0° C. The reaction mixture was allowed to warm to room temperature and stirred for 1 h, then treated with hydrochloric acid (5M) to pH2–3. The resulting mixture was extracted with ethyl acetate (2×1000 ml) and the combined extracts were washed with brine (1000 ml), dried (Na$_2$SO$_4$) and evaporated in vacuo to give the title compound as a brown oil (46.1 g).

Mass spectrum (API$^-$): 243 (M—H)$^-$ C$_{15}$H$_{16}$O$_3$ requires 244.

$^1$H NMR (CDCl$_3$) δ: 2.03 (1H, m), 2.36 (1H, m), 2.62 (2H, m), 2.95 (1H, m), 3.92 (3H, s), 5.02 (2H, m), 5.76 (1H, m), 7.07 (2H, m), 7.20 (1H, m), 7.69 (1H, d, J=9 Hz), 13.41 (1H, s).

DESCRIPTION 11

3-(2-Propenyl)-2-tetralone

A mixture of 3,4-dihydro-2-hydroxy-3-(2-propenyl)-naphthalene carboxylic acid, methyl ester (46.1 g, crude), dimethyl sulphoxide (132 ml), water (5 ml) and lithium chloride (9.5 g, 226 mmol) was heated at 125° C., with stirring, under argon for 4.5 h. The mixture was cooled and diluted with water (750 ml) and extracted with ethyl acetate (3×1000 ml). The combined extracts were washed with water (1000 ml) and brine (1000 ml), dried (Na$_2$SO$_4$) and evaporated in vacuo to give a brown oil (35.5 g). This was chromatographed on silica eluting with 10% ether-hexane to give the title compound as a brown oil (25.9 g, 74%).

Mass spectrum (API$^-$): 185 (M—H)$^-$. C$_{13}$H$_{14}$O requires 186.

$^1$H NMR (CDCl$_3$) δ: 2.14 (1H, m), 2.54 (2H, m), 2.84 (1H, m), 3.08 (1H, m), 3.60 (2H, d, J=3 Hz), 5.08 (2H, m), 5.79 (1H, m), 7.16 (4H, m).

DESCRIPTION 12

3-(2-Propenyl)-2-tetralone Ethylene Ketal

A mixture of 3-(2-propenyl)-2-tetralone (25.9 g, 139 mmol), trimethyl orthoformate (61.3 ml, 554 mmol), ethanediol (57.5 ml, 1.03 mol), p-toluenesulfonic acid monohydrate (0.27 mg, 1.4 mmol) in dichloromethane (650 ml) was stirred at room temperature, under argon for 2 h. Resulting mixture was partitioned between saturated aqueous sodium bicarbonate (1000 ml) and dichloromethane (3×500 ml). The combined organic extracts were washed with brine (500 ml), dried (Na2SO$_4$) and evaporated in vacuo to give a brown oil (34.9 g). Chromatography on silica using 0–10% ether-hexane gradient elution gave the title compound as a yellow oil (20.1 g, 63%).

¹H NMR (CDCl₃) δ: 1.91 (1H, m), 2.07 (1H, m), 2.53 (1H, m), 2.77 (1H, m), 2.99 (3H, m), 4.02 (4H, m), 5.04 (2H, m), 5.83 (1H, m), 7.08 (4H, m).

DESCRIPTION 13
2-Oxo-1,2,3,4-tetrahydronaphthalene-3-acetic Acid, Methyl Ester Potassium permanganate (1.71 g, 11 mmol) was added to a stirred solution of sodium periodate (35.3 g, 165 mmol) in water (600 ml) at room temperature. After 0.5 h, potassium carbonate (4.58 g, 33 mmol) was added. After 0.25 h, tert-butanol (180 ml) was added dropwise followed by 3-(2-propenyl)-2-tetralone ethylene ketal (4.21 g, 18 mmol) in tert-butanol (180 ml). After 3 h, the reaction mixture was cooled to 0 °C. and sodium metabisulfite added until the pink solution turned brown. The resulting mixture was diluted with water (300 ml) and extracted with dichloromethane (2×500 ml). The combined extracts were washed with water (500 ml), and brine (500 ml), then dried (Na₂SO₄), and the solvent evaporated in vacuo to give a yellow oil (4.64 g), that was dissolved in acetonitrile (90 ml) and methanolic hydrochloric acid (90 ml), and stirred at room temperature under argon. After 3 h, water (20 ml) was added, and the mixture stirred for 2 h. The resultant mixture was evaporated in vacuo and the residue was partitioned between water (50 ml) and ethyl acetate (2×100 ml). Combined extracts were washed with brine (100 ml), dried (Na₂SO₄) and the solvent evaporated in vacuo to give the title compound as a yellow oil (3.62 g, 91%).

¹H NMR (CDCl₃) δ: 2.56 (1H, m), 2.87 (2H, m), 3.05 (2H, m), 3.66 (2H, s), 3.70 (3H, s), 7.16 (4H, m).

DESCRIPTION 14
cis-1-Benzyl-1,3,3a,4,9,9a-hexahydro-2H-benz[f]indole-2-one

Acetic acid (12.5 ml) was added to a stirred mixture of 2-oxo-1,2,3,4-tetrahydronaphthalene-3-acetic acid methyl ester (3.62 g, 17 mmol), and benzylamine (7.2 ml, 66 mmol) in a 1:1 mixture of tetrahydrofuran and methanol (120 ml) at 0° C. under argon. After 0.5 h, sodium cyanoborohydride (2.09 g, 33 mmol) was added and the resultant mixture stirred at room temperature. After 16 h, aqueous 10% sodium hdyroxide was added and the solvent evaporated in vacuo. The residue was partitioned between water (100 ml) and dichloromethane (2×200 ml). The combined extracts were washed with water (100 ml), brine (100 ml), then dried (Na₂SO₄) and evaporated in vacuo to give a brown solid (4.38 g). Chromatography on silica using 0–5% methanol-ethyl acetate gradient elution afforded the title compound as a yellow solid (1.75 g, 38%).

Mass spectrum (API⁺): 278 (MH⁺). C₁₉H₁₉NO requires 277.

¹H NMR (CDCl₃) δ: 2.14 (1H, m), 2.57 (1H, m), 2.75 (5H, m), 3.86 (1H, m), 4.07 (1H, d, J=16 Hz), 4.89 (1H, d, J=16 Hz), 6.95 (1H, d, J=2 Hz), 7.15 (3H, m) 7.30 (5H, m).

DESCRIPTION 15
cis-1-Benzyl-2,3,3a,4,9,9a-hexahydro-1H-benz[f]indole

To a stirred suspension of lithium aluminium hydride (0.96 g, 25 mmol) in dry tetrahydrofuran (30 ml) at 0° C. under argon, was added cis-1-benzyl-1,3,3a,4,9,9a-hexahydro-2H-benz[f]indol-2-one (1.75 g, 6 mmol) in dry tetrahydrofuran (5 ml). The resultant mixture was then heated at reflux for 6 h, cooled to 0° C. and, with vigorous stirring, water (1 ml) was added, followed by aqueous 10% sodium hydroxide (5 ml) and water (2 ml). The resultant mixture was filtered and the solid residue was washed with dichloromethane (10 ml). The filtrate was dried (Na₂SO₄) and the solvent evaporated in vacuo to give the title compound as a yellow oil (1.2 g, 72%).

Mass spectrum (API⁺): 264 (MH⁺). C₁₉H₂₁N requires 263.

¹H NMR (CDCl₃) δ: 1.39 (1H, m), 1.90 (1H, m), 2.12 (1H, m), 2.34–2.63 (3H, br m), 2.78 (4H, m), 3.39 (1H, d, J=13 Hz), 3.99 (1H, d, J=13 Hz), 7.12 (4H, m), 7.26 (5H, m).

DESCRIPTION 16
cis-2,3,3a,4,9,9a-Hexahydro-1H-benz[f]indole

A mixture of cis-1-benzyl-2,3,3a,4,9,9a-hexahydro-1H-benz[f]indole (1.20 g, 4.6 mmol) and palladium hydroxide (0.91 g, 8.6 mmol) in degassed methanol (90 ml) was hydrogenated at 50° C. and 50 psi pressure for 5 h. The resultant mixture was cooled and filtered through kieselguhr. The filtrate was evaporated in vacuo to give the title compound as a colourless oil (0.55 g, 70%).

Mass spectrum (API⁺): 174 (MH⁺). C₁₂H₁₅N required 173.

¹H NMR (CDCl₃) δ: 1.26 (1H, m), 2.00 (1H, m), 2.40–2.92 (8H, br m), 3.52 (1H, m), 7.14 (4H, m).

DESCRIPTION 17
cis-2,3,3a,4,9,9a-Hexahydro-5-methoxy-1H-benz[f]indole

Prepared from 5-methoxy-2-tetralone using a procedure similar to that of Descriptions 9 to 16 inclusive.

Mass spectrum (API⁺): 204 (MH⁺). C₁₃H₁₇NO requires 203.

¹H NMR (CDCl₃) δ: 2.00 (1H, m), 2.15–2.95 (9H, m), 3.82 (3H, s), 6.75 (2H, m), 7.12 (1H, t, J=8 Hz).

DESCRIPTION 18
N-(4-Hydroxybutyl)-4-phenylbenzamide

To a stirred solution of 4-amino-1-butanol (7.34 g, 82 mmol) and triethylamine (12.3 ml; 8.82 g, 87 mmol) in dichloromethane (100 ml) at 0° C. was added a solution of 4-phenylbenzoyl chloride (18.36 g, 85 mmol) in dichloromethane (800 ml) dropwise over 1.2 h. Resultant was stirred at 0° C. for 2 h then at room temperature for 18 h. The resulting white solid was filtered off (15.94 g) and the filtrate washed with 5% aqueous sodium hydroxide (1L). The organic phase was dried (Na₂SO₄) and evaporated in vacuo to give a white solid (4.96 g) which was combined with the above to give the title compound (20.9 g, 93%).

¹H NMR (DMSO-d₆) δ: 1.4–1.7 (4H, m), 3.26 (2H, q, J=7 Hz), 3.42 (2H, q, J=7 Hz), 4.43 (1H, t, J=6 Hz), 7.35–7.55 (3H, m), 7.75 (4H, m), 7.94 (2H, d, J=9 Hz), 8.52 (1H, t, J=7 Hz).

DESCRIPTION 19
4-(4-Phenylbenzoylamino)butyraldehyde

To a mechanically-stirred solution of N-(4-hydroxybutyl)-4-phenylbenzamide (11.2 g, 44.2 mmol) and triethylamine (148 ml; 107.5 g, 1.06 mol) in dimethyl sulfoxide (250 ml) at room temperature was added, dropwise over 1 h, a solution of pyridine-sulfur trioxide complex (43.7 g, 0.273 mol) in dimethyl sulfoxide (200 ml) with external cooling using a cold water bath. The mixture was stirred at room temperature for 3 h, then 2M hydrochloric acid (550 ml) was added slowly with ice cooling. Resultant was diluted with water (1L) then extracted with ethyl acetate (3×500 ml). The combined extracts were washed with 2M hydrochloric acid (3×500 ml) and water (3×500 ml) then dried (Na2SO4) and evaporated in vacuo to give a semi solid (12 g). Chromatography on silica gel eluting with 10–100% ethyl acetate-hexane gave the title compound as a white solid (4.72 g, 42%).

¹H NMR (CDCl₃) δ: 2.00 (2H, m), 2.65 (2H, m), 3.52 (2H, q, J=8 Hz), 6.54 (1H, br m), 7.35–7.53 (3H, m), 7.54–7.71 (4H, m), 7.85 (2H, m), 9.83 (1H, s).

DESCRIPTION 20

(±)-trans-2-(1-(1,2,3,4-Tetrahydro-2-(4-toluene)sulfonamido)naphthyl)malonic Acid, Diethyl Ester Sodium (0.33 g, 14 mg atoms) was added to ethanol (36 ml) with stirring. After 0.6 h, dimethyl malonate (2.1 g, 15 mmol) was added in one portion. Resultant was stirred for 0.25 h, then (±)-1a,2,3,7b-tetrahydro-1-(4-toluene)sulfonyl-1H-naphth[1,2-b]azirine (D. A. Evans et al., J. Org. Chem, 1991 56 6744) (4.0 g, 13 mmol) was added. The mixture was stirred at 20° C. for 2.5 h, then poured into water (400 ml) and extracted with ethyl acetate (3×200 ml). Combined organic extracts were dried ($Na_2SO_4$) and evaporated in vacuo to give the title compound (6.2 g, 100%).

$^1$H NMR ($CDCl_3$) δ: 1.00 and 1.27 (6H, 2×t, J=8 Hz), 1.77–2.08 (2H, m), 2.44 (3H, s), 2.82 (2H, t, J=7 Hz), 3.44 (2H, m), 3.90 and 4.17 (4H, 2×m), 4.44 (1H, d, J=9 Hz), 6.92–7.21 (3H, m), 7.34 (2H, d, J=9 Hz), 7.76 (2H, d, J=9 Hz).

The following compound was prepared in a similar manner to description 20

(a) (±)-trans-2-(1-(5-Methoxy-1,2,3,4-tetrahydro-2-(4-toluene)sulfonamido)naphthyl)malonic Acid, Diethyl Ester $^1$H NMR ($CDCl_3$) δ: 1.03 & 1.28 (6H, 2×t, J=8 Hz), 1.91 (2H, m), 2.45 (3H, s), 2.67 (2H, m), 3.39 (2H, m), 3.82 (3H, s), 3.86–4.02 (2H, m), 4.22 (2H, m), 4.44 (1H, d, J=9 Hz), 6.57 (1H, d, J=8 Hz), 6.73 (1H, d, J=8 Hz), 7.05 (1H, t, J=8 Hz), 7.32 (2H, d, J=9 Hz), 7.76 (2H, d, J=9 Hz).

DESCRIPTION 21

(±)-trans-2-(1-(1,2,3,4-Tetrahydro-2-(4-toluene)sulfonamido)naphthyl)acetic Acid A mixture of (±)-trans-2-(1-(1,2,3,4-tetrahydro-2-(4-toluene)sulfonamido)-napthyl)malonic acid, diethyl ester (6.2 g, 13.5 mmol), ethanol (300 ml), potassium hydroxide (20 g, 0.35 mol) and water (145 ml) was heated at reflux for 3 h, then concentrated in vacuo to 100 ml. The mixture was acidified (pH1) with hydrochloric acid (5M), then dichloromethane (100 ml) was added. Resulting solid was filtered off (4.9 g), then heated with xylene (100 ml) at reflux for 4 h. The mixture was cooled, then evaporated in vacuo to give the title compound (3.6 g, 74%).

$^1$H NMR (DMSO-$d_6$) δ: 1.58 (2H, m), 2.40 (3H, s), 2.46 (1H, m), 2.52–2.83 (3H, m), 3.09 (1H, m), 3.45 (1H, m), 6.90–7.12 (4H, m), 7.38 (2H, d, J=9 Hz), 7.66 (1H, d, J=9 Hz), 7.72 (2H, d, J=9 Hz).

The following compound was prepared in a similar manner to description 21

(a) (±)-trans-2-(1-(5-Methoxy-1,2,3,4-tetrahydro-2-(4-toluene)sulfonamido)naphthyl)acetic Acid $^1$H NMR ($CD_3OD$) δ: 1.59–1.84 (2H, m), 2.46 (3H, s), 2.48–2.77 (4H, m), 3.11 (1H, m), 3.60 (1H, m), 3.79 (3H, s), 6.71 (2H, m), 7.08 (1H, t, J=8 Hz), 7.37 (2H, d, J=9 Hz), 7.77 (2H, d, J=9 Hz).

DESCRIPTION 22

(±)-trans-2-(1-(1,2,3,4-Tetrahydro-2-(4-toluene)sulfonamido)naphthyl)ethanol

To a stirred solution of (±)-trans-2-(1-(1,2,3,4-tetrahydro-2-(4-toluene)sulfonamido)naphthyl)acetic acid (3.6 g, 10 mmol) in dry tetrahydrofuran (110 ml) was added lithium aluminium hydride (2.9 g, 76 mmol), portionwise over 0.2 h. Mixture was stirred at room temperature for 0.5 h, then at reflux for 4 h. Resultant was cooled, then water (0.5 ml), followed by aqueous NaOH (10%; 2 ml) and water (1.0 ml) was added sequentially with ice cooling. The supernatant liquid was decanted and the precipitate extracted exhaustively with dichloromethane. The organic solutions were combined, dried ($Na_2SO_4$) and evaporated in vacuo to give the title compound (2.98 g, 86%) as an oil.

Mass spectrum (API$^+$): Found 346 (MH$^+$). $C_{19}H_{23}NO_3S$ requires 345.

$^1$H NMR ($CDCl_3$) δ: 1.45–2.00 (5H, m), 2.44 (3H, s), 2.76 (3H, m), 3.65 (2H, t, J=8 Hz), 3.70 (1H, m), 6.93–7.17 (5H, m), 7.34 (2H, d, J=9 Hz), 7.77 (2H, d, J=9 Hz).

The following compound was prepared in a similar manner to description 22

(a) (±)-trans-2-(1-(5-Methoxy-1,2,3,4-tetrahydro-2-(4-toluene)sulfonamido)naphthyl)ethanol $^1$H NMR ($CDCl_3$) δ: 1.52–1.96 (5H, m), 2.43 (3H, s), 2.52–2.84 (3H, m), 3.66 (3H, m), 3.80 (3H, s), 4.66 (1H, d, J=9 Hz), 6.65 (2H, m), 7.10 (1H, t, J=8 Hz), 7.31 (2H, d, J=8 Hz), 7.76 (2H, d, J=8 Hz).

DESCRIPTION 23

(±)-trans-2,3,3a,4,5,9b-Hexahydro-3-(4-toluene)sulfonyl-1H-benz[e]indole

To a mixture of (±)-trans-2-(1-(1,2,3,4,-tetrahydro-2-(4-toluene)sulfonamido)naphthyl)ethanol (2.9 g, 8.4 mmol), triethylamine (3.8 ml; 27 mmol) and dichloromethane (100 ml) at 4° C. under argon was added methanesulfonyl chloride (0.7 ml; 9 mmol). The mixture was stirred at 20° C. for 2 h then partitioned between dichloromethane (50 ml) and saturated aqueous $NaHCO_3$ (150 ml). Organic phase was dried ($Na_2SO_4$) and evaporated in vacuo to give an oil (3.7 g) which was dissolved in methanol (200 ml) and treated with anhydrous potassium carbonate (3.6 g, 26 mmol). Reaction mixture was stirred at 20° C. for 16 h then evaporated in vacuo. Residue was partitioned between water (100 ml) and dichloromethane (3×50 ml) and the combined organic extracts were dried ($Na_2SO_4$) and evaporated in vacuo to give a solid (2.3 g). Chromatography on silica with 15–50% ethyl acetate-hexane gradient elution gave the title compound (1.85 g, 67%) as a solid.

Mass spectrum (API$^+$): Found 328 (MH$^+$). $C_{19}H_{21}NO_2S$ requires 327.

$^1$H NMR ($CDCl_3$) δ: 1.49 (1H, m), 2.02 (1H, m), 2.33 (1H, m), 2.40 (3H, s), 2.71–2.92 (2H, m), 2.93–3.17 (3H, m), 3.53 (1H, t, J=10 Hz), 3.68 (1H, m), 6.95 (1H, d, J=9 Hz), 7.11 (3H, m), 7.30 (2H, d, J=9 Hz), 7.69 (2H, d, J=9 Hz).

The following compounds were prepared in a similar manner to description 23

(a) (±)-trans-2,3,3a,4,5,9b-Hexahydro-6-methoxy-3-(4-toluene)sulfonyl-1H-benz[e]indole Mass spectrum (API$^+$): Found 358 (MH$^+$). $C_{20}H_{23}NO_3S$ requires 357

(b) (4aS, 10bS)-trans-7-Methoxy-1,2,3,4,4a,5,6,10b-octahydro-4-(4-toluene)sulfonylbenzo[f]quinoline $^1$H NMR ($CDCl_3$) δ: 1.15–1.34 (1H, m), 1.79–2.08 (3H, m), 2.29–2.66 (3H, m), 2.44 (3H, s), 2.73–3.04 (4H, m), 3.79 (3H, s), 4.27 (1H, dt, J=9 Hz), 6.67 (1H, d, J=9 Hz), 6.85 (1H, d, J=9 Hz), 7.13 (1H, t, J=9 Hz), 7.30 (2H, d, J=9 Hz), 7.73 (2H, d, J=9 Hz).

DESCRIPTION 24

(±)-trans-2,3,3a,4,5,9b-Hexahydro-1H-benz[e]indole

A mixture of (±)-trans-2,3,3a,4,5,9b-hexahydro-3-(4-toluene)sulfonyl-1H-benz[e]indole (1.15 g, 3.5 mmol), lithium aluminium hydride (0.84 g, 22 mmol) and tetrahydrofuran (40 ml) was heated at reflux under argon for 20 h. The mixture was cooled then treated dropwise with water (1 ml), aqueous NaOH (10%; 3 ml) and water (1 ml) with ice cooling. Dichloromethane (150 ml) was added and the supernatant liquid was decanted, dried ($Na_2SO_4$) and evaporated in vacuo to give the title compound (0.62 g, 100%) as an oil.

Mass spectrum (API+): Found 174 (MH+) C₁₂H₁₅N requires 173.

¹H NMR (CDCl₃) δ: 1.64–1.87 (2H, m), 2.04 (1H, br s), 2.27 (1H, m), 2.44 (1H, m), 2.63 (1H, m), 2.79 (1H, dt, J=11, 4 Hz), 3.04 (2H, m), 3.25 (2H, m), 7.12 (4H, s).

The following compounds were prepared in a similar manner to description 24

(a) (±)-trans-2,3,3a,4,5,9b-Hexahydro-6-methoxy-1H-benz[e]indole

Mass spectrum (API+): Found 204 (MH+). C₁₃H₁₇NO requires 203.

(b) (4aS, 10bS)-trans-7-Methoxy-1,2,3,4,4a,5,6,10b-octahydrobenzo[f]quinoline

Mass spectrum (API+): Found 218 (MH+). C₁₄H₁₉NO requires 217.

¹H NMR (CDCl₃) δ: 1.27 (1H, m), 1.58–1.98 (5H, m), 2.35–2.79 (5H, m), 2.96 (1H, dd, J=17, 6 Hz), 3.15 (1H, m), 3.82 (3H, s), 6.70 (1H, d, J=9 Hz), 6.93 (1H, d, J=9 Hz), 7.16 (1H, t, J=9 Hz). HPLC (Chiralcel OD, hexane/ethanoldiethylamine 90:10:0.1): chiral purity 93.3%

DESCRIPTION 25

(1aS, 7bR)-4-Methoxy-1a,2,3,7b-tetrahydro-1-(4-toluene)sulfonyl-1H-naphth[1,2-b]azirine A mixture of (S,S)-1,2-cyclohexanediamine-bis-(2,6-dichloro)benzylidineimine (4.7 g, 11 mmol), copper (I) trifluoromethylsulfonate benzene complex (2.7 g, 5.4 mmol) and dichloromethane (540 ml) was stirred at 25° C. for 1 h under argon. The mixture was filtered and to the filtrate was added 1,2-dihydro-8-methoxynaphthalene (5.4 g, 34 mmol). The mixture was stirred at 25° C. for 0.25 h, then cooled to −68° C., whereupon (N-(4-toluenesulfonyl)imino)phenyliodinane (80% pure; 17.0 g, 46 mmol) was added in one portion. The mixture was stirred at −68° C. to −64° C. for 6 h then warmed to 25° C. over 16 h. The reaction mixture was filtered through silica (40 g) with dichloromethane elution, and the combined fractions were evaporated in vacuo. Chromatography of the residue on silica with 10–20% ethyl acetate-hexane gradient elution gave the title compound (7.3 g, 66%) as a solid.

Stereochemistry assigned as 1aS, 7bR based on analogy with aziridination of 1,2-dihydronaphthalene (Z. Li et al; J. Am. Chem. Soc. 1993, 115, 5326).

HPLC (Chiralcel OJ, hexane/ethanol 1:1): chiral purity 83.1%.

DESCRIPTION 26

(1S, 2S)-trans-5-Methoxy-1-(3-propenyl)-1,2,3,4-tetrahydro-2-(4-toluene)sulfonamidonaphthalene To a solution of (1aS, 7bR)-4-methoxy-1a,2,3,7b-tetrahydro-1-(4-toluene)sulfonyl-1H-naphth[1,2-b]azirine (as prepared in description 25) (9.8 g, 30 mmol) in dry ether (600 ml) under argon was added a solution of allylmagnesium bromide in ether (1M; 84 ml; 84 mmol) at 10° C. Mixture was stirred at 25° C. for 17 h then poured into aqueous citric acid (10%; 200 ml). Resultant was extracted with ether (2×100 ml) and the combined organic extracts were dried (Na₂SO4) and evaporated in vacuo. Chromatography of the residue on silica using 3:1 hexane-ethyl acetate as eluant gave a solid (11.5 g), which was recrystallised twice from hexane-ethyl acetate to give the title compound (3.8 g, 33%) as colourless needles.

Mass spectrum (API+): Found 372 (MH+). C₂₁H₂₅NO₃S requires 371.

¹H NMR (CDCl₃) δ: 1.77 (2H, m), 2.14 (1H, m), 2.32 (1H, m), 2.44 (3H, s), 2.56 (2H, m), 2.72 (1H, ddd, J=16, 7, 3 Hz), 3.73 (1H, m), 3.81 (3H, s), 4.48 (1H, d, J=8 Hz), 4.89–5.05 (2H, m), 5.57 (1H, m), 6.62 (1H, d, J=9 Hz), 6.68 (1H, d, J=9 Hz), 7.11 (1H, t, J=9 Hz), 7.32 (2H, d, J=9 Hz), 7.75 (2H, d, J=9 Hz).

HPLC (Chiralcel OD, hexane/ethanol 9:1): chiral purity 99.5%.

DESCRIPTION 27

(1S, 2S)-trans-3-(1-(1,2,3,4,-Tetrahydro-2-(4-toluene)sulfonamido)naphthyl)propanol To a stirred solution of (1S, 2S)-trans-5-methoxy-1-(3-propenyl)-1,2,3,4-tetrahydro-2-(4-toluene)sulfonamidonaphthalene (3.55 g, 10 mmol) in dry tetrahydrofuran (150 ml) at 25° C. under argon was added, dropwise over 0.1 h a solution of borane in tetrahydrofuran (1M; 11 ml, 11 mmol). The mixture was stirred at 25° C. for 18 h, then aqueous NaOH (10%; 14 ml; 35 mmol) was added, followed by aqueous hydrogen peroxide (27%; 5 ml; 39.5 mmol). The mixture was stirred at 25° C. for 2 h, then water (350 ml) was added and the resulting mixture extracted with dichloromethane (3×120 ml). Combined extracts were dried (Na₂SO₄) then evaporated in vacuo. Chromatography of the residue on silica with 20–100% ethyl acetate-hexane gradient elution gave the title compound (2.15 g, 58%).

¹H NMR (CDCl₃) δ: 1.27 (1H, br s), 1.39–1.64 (4H, m), 1.65–1.90 (2H, m), 2.45 (3H, s), 2.55 (2H, m), 2.64 (1H, m), 3.54 (2H, m), 3.67 (1H, m), 3.81 (3H, s), 4.54 (1H, d, J=10 Hz), 6.60 (1H, d, J=9 Hz), 6.68 (1H, d, J=9 Hz), 7.11 (1H, t, J=9 Hz), 7.33 (2H, d, J=9 Hz), 7.75 (2H, d, J=9 Hz).

EXAMPLE 1 trans-7-Methoxy-4-(4-(4-phenylbenzoylamino)butyl)-1,2,3,4,4a,5,6,10b-octahydrobenzo[f]quinoline Sodium triacetoxyborohydride 0.83 g, 3.9 mmol) was added to a stirred mixture of trans-7-methoxy-1,2,3,4,4a,5,6,10b-octahydrobenzo[f]quinoline (D6a, 0.57 g, 2.6 mmol) and 4-(4-phenylbenzoylamino)butyraldehyde (0.77 g, 2.9 mmol) in dichloromethane (50 ml) at room temperature. After stirring for 6 h, the mixture was poured onto saturated aqueous K₂CO₃ (40 ml) and extracted with dichloromethane (3×20 ml). The combined organic extracts were washed with brine, dried (Na₂SO4) and concentrated in vacuo to afford a white solid which was chromatographed on silica using 40–100% ethyl acetate/pentane as elution gradient. The title compound was obtained as a white solid (1.2 g, 99%).

Mass Spectrum (API+): 469 (MH+, 100%) C₃₁H₃₆N₂O₂ requires 468.

¹H NMR (CDCl₃) δ: 1.12–1.32 (1H, m), 1.42–1.78 (7H, m), 2.13–2.73 (7H, m), 2.86 –3.19 (3H, m), 3.46–3.57 (2H, m), 3.80 (3H, s), 6.62–6.80 (2H, m), 6.90 (1H, d, J=6.6 Hz), 7.10–7.19 (1H, m), 7.31–7.69 (7H, m), 8.86 (2H, d, J=6.6 Hz).

The following compounds were prepared in a similar manner to Example 1

(a) (±)-trans-8-Methoxy-4-(4-(4-phenylbenzoylamino)butyl)-1,2,3,4,4a,5,6,10b-octahydrobenzo[f]quinoline Mass spectrum (API+): Found 469 (MH+). C₃₁H₃₆N₂O₂ requires 468.

¹H NMR (CDCl₃) δ: 1.13 (1H, m), 1.56 (1H, m), 1.66 (6H, m), 1.77 (2H, m), 2.11 (1H, dt, J=10, 3 Hz), 2.22 (2H, m), 2.45 (1H, m), 2.55 (1H, m), 2.85 (1H, m), 2.90 (1H, m), 3.07 (1H, m), 3.53 (2H, m), 3.76 (3H, s), 6.60 (1H, d, J=3 Hz), 6.69 (2H, m), 7.16 (1H, d, J=9 Hz), 7.37 (1H, m), 7.45 (2H, t, J=9 Hz), 7.59 (4H, m), 7.84 (2H, m).

(b) (±)-trans-2,3,3a,4,5,9b-Hexahydro-3-(4-(4-phenylbenzoylamino)butyl)-1H-benz[e]indole Mass spectrum (API+): Found 425 (MH+). C₂₉H₃₂N₂N₂O requires 424. ¹H NMR (CDCl₃) δ: 1.53–1.85 (6H, m), 2.17 (3H, m), 2.35 (2H, m), 2.89 (3H, m), 3.05 (1H, dd, J=16, 9 Hz), 3.49 (3H, m), 6.97 (1H, m), 7.04 (1H, m), 7.13 (3H, m), 7.38 (1H, m), 7.44 (2H, t, J=9 Hz), 7.55 (2H, d, J=9 Hz), 7.62 (2H, d, J=9 Hz), 7.85 (2H, d, J=9 Hz).

(c) (±)-trans-2,3,3a,4,5,9b-Hexahydro-6-methoxy-3-(4-(4-phenylbenzoylamino)butyl-1H-benz[e]indole Mass spectrum (API$^+$): Found 455 (MH$^+$). $C_{30}H_{34}N_2O_2$ requires 454.

hu 1H NMR (CDCl$_3$) δ: 1.58–1.86 (6H, m), 2.16 (3H, m), 2.34 (2H, m), 2.76 (1H, m), 2.90 (3H, m), 3.47 (3H, m), 3.82 (3H, s), 6.69 (2H, m), 6.83 (1H, m), 7.14 (1H, t, J=8 Hz), 7.42 (3H, m), 7.56 (2H, d, J=8 Hz), 7.63 (2H, d, J=9 Hz), 7.83 (2H, d, J=9 Hz).

(d) (4aS, 10bS)-trans-7-Methoxy-4-(4-(4-phenylbenzoylamino)butyl)-1,2,3,4,4a,5,6,10b-octahydrobenzo[f]quinoline Mass spectrum (API$^+$): Found 469 (MH$^+$). $C_{31}H_{36}N_2O_2$ requires 468.

$^1$H NMR (CDCl$_3$) δ: 1.25 (1H, m), 1.54 (1H, m), 1.69 (4H, m), 1.81 (2H, m), 2.04–2.40 (5H, m), 2.50 (2H, m), 2.65 (1H, m), 2.94 (1H, m), 3.13 (1H, m), 3.52 (2H, m), 3.81 (3H, s), 6.70 (1H, d, J=9 Hz), 6.80 (1H, m), 6.91 (1H, d, J=9 Hz), 7.14 (1H, t, J=9 Hz), 7.44 (3H, m), 7.61 (4H, m), 7.86 (2H, d, J=9 Hz).

HPLC (Chiralcel OD, hexane/ethanol/TFA 90:10:0.1): chiral purity 99.4%.

EXAMPLE 2 cis-7-Methoxy-4-(4-(4-phenylbenzoylamino)butyl)-1,2,3,4,4a,5,6,10b-octahydrobenzo[f]quinoline Sodium triacetoxyborohydride (1.5 g, 6.9 mmol) was added to a stirred mixture of cis-7-methoxy-1,2,3,4,4a,5,6,10b-octahydrobenzo[f]quinoline (D6b, 1.0 g, 4.6 mmol) and 4-(4-phenylbenzoylamino)butyraldehyde (1.4 g, 5.1 mmol) in dichloroethane (50 ml) at room temperature. After stirring for 12 h, saturated aqueous K$_2$CO$_3$ (40 ml) was added and the mixture extracted into dichloromethane (3×20 ml). The combined organic extracts were washed with brine, dried (Na2SO$_4$) and concentrated in vacuo to give a gum. Chromatography on silica, using 50–100% ethyl acetate/pentane as elution gradient, gave the title compound as a white solid (1.29 g, 60%).

Mass Spectrum (API$^+$): 469 (MH$^+$, 100%) $C_{31}H_{36}N_2O_2$ requires 468.

$^1$H NMR (CDCl$_3$) δ: 1.55–1.93 (10H, m), 2.35–2.68 (4H, m), 2.81–3.15 (4H, m), 3.41–3.55 (2H, m), 3.78 (3H, s), 6.58–6.75 (3H, m), 7.01–7.12 (1H, m), 7.42–7.67 (7H, m), 7.82 (2H, d, J=6.6 Hz).

EXAMPLE 3 trans-7-Hydroxy-4-(4-(4-phenylbenzoylamino)butyl)-1,2,3,4,4a,5,6,10b-octahydrobenzo[f]quinoline To a stirred solution of trans-7-methoxy-4-(4-(4-phenylbenzoylamino)butyl)-1,2,3,4,4a,5,6,10b-octahydrobenzo[f]quinoline (E1, 1.1 g, 2.4 mol) in dichloromethane (30 ml) at 0° C. was added a 1M solution of boron tribromide in dichloromethane (7.1 ml, 7.1 mmol). The mixture was allowed to warm to room temperature and stirred for a further 72 h before pouring onto crushed ice (100 ml) and 0.880 ammonia (100 ml) and extracting into dichloromethane (3×30 ml). The combined extracts were dried (Na$_2$SO$_4$) and evaporated in vacuo to afford a brown solid (440 mg, 40%).

Mass Spectrum (API$^+$): 455 (MH$^+$, 100%) $C_{30}$H34NO$_2$O$_2$ requires 454.

$^1$H NMR (CDCl$_3$) δ: 1.46–1.90 (8H, m), 2.11–2.72 (7H, m), 2.82–3.17 (4H, m), 3.45–3.60 (2H, m), 6.57–6.70 (2H, m), 6.84–6.91 (1H, m), 7.0–7.10 (1H, m), 7.34–7.70 (7H, m), 7.85 (2H, d, J=6.6 Hz).

The following compounds were prepared in a similar manner to example 3

(a) (±)-trans-8-Hydroxy-4-(4-(4-phenylbenzoylamino)butyl)-1,2,3,4,4a,5,6,10b-octahydrobenzo[f]quinoline Mass spectrum (API$^+$): Found 455 (MH$^+$). $C_{30}H_{34}N_2O_2$ requires 454.

$^1$H NMR (CDCl$_3$) δ: 1.22 (1H, m), 1.46–1.90 (9H, m), 2.19 (2H, m), 2.30–2.67 (3H, m), 2.75 (1H, s), 2.90 (1H, m), 3.09 (1H, m), 3.50 (2H, m), 6.56 (1H, d, J=3 Hz), 6.66 (1H, dd, J=9, 3 Hz), 6.75 (1H, m), 7.09 (1H, d, J=9 Hz), 7.44 (3H, m), 7.60 (4H, m), 7.84 (2H, d, J=9 Hz).

(b) (±)-trans-2,3,3a,4,5,9b-Hexahydro-6-hydroxy-3-(4-(4-phenylbenzoylamino)butyl)-1H-benz[e]indole Mass spectrum (API$^+$): Found 441 (MH$^+$). $C_{29}H_{32}N_2O_2$ requires 440.

$^1$H NMR (CDCl$_3$) δ: 1.50–1.83 (8H, m), 2.11 (1H, m), 2.20–2.44 (3H, m), 2.61–2.87 (2H, m), 2.95 (2H, m), 3.48 (3H, m), 6.64 (2H, d, J=8 Hz), 6.77 (1H, m), 7.03 (1H, t, J=9 Hz), 7.41 (3H, m), 7.57 (2H, d, J=8 Hz), 7.63 (2H, d, J=9 Hz), 7.83 (2H, d, J=9 Hz).

(c) (4aS, 10bS)-trans-7-Hydroxy-4-(4-phenylbenzoylamino)butyl)-1,2,3,4,4a,5,6,10b-octahydrodrobenzo[f]quinoline Mass spectrum (API$^+$): Found 455 (MH$^+$). $C_{30}H_{34}N_2O_2$ requires 454.

$^1$H NMR (CDCl$_3$) δ: 1.22 (1H, m), 1.45–1.85 (7H, m), 2.05–2.69 (7H, m), 2.90 (2H, m), 3.06 (1H, m), 3.52 (2H, m), 6.66 (2H, m), 6.85 (1H, d, J=9 Hz), 7.04 (1H, t, J=9 Hz), 7.42 (3H, m), 7.60 (4H, m), 7.83 (2H, d, J=9 Hz).

EXAMPLE 4 cis-7-Hydroxy-4-(4-(4-phenylbenzoylamino)butyl)-1,2,3,4,4a,5,6,10b-octahydrobenzo[f]quinoline To a stirred solution of cis-7-methoxy-4-(4-(4-phenylbenzoylarino)butyl)-1,2,3,4,4a,5,6,10b-octahydrobenzo[f]quinoline (E2, 1.0 g, 2.1 mmol) in dichloromethane (5 ml) at 0° C. was added a 1M solution of boron tribromide in dichloromethane (6.4 ml, 6.4 mmol). The mixture was allowed to warm to room temperature and stirred for a further 72 h, then poured onto crushed ice (50 ml) and 0.880 ammonia (50 ml) and extracted with dichloromethane (3×30 ml). The combined extracts were dried (Na$_2$SO$_4$) and evaporated in vacuo to give a brown solid (720 mg, 76%).

Mass Spectrum (API$^+$): 455 (MH$^+$, 100%) $C_{30}H_{34}N_2O_2$ requires 454.

$^1$H NMR (CDCl$_3$) δ: 1.54–2.0 (9H, m), 2.35–2.68 (5H, m), 2.52–3.16 (2H, m), 3,45–3.55 (2H, m), 3.80 (3H, s), 6.60–6.77 (3H, m), 7.01–7.12 (1H, m), 7.32–7.67 (7H, m), 7.81 (2H, d, J=6.6 Hz).

EXAMPLE 5 trans-7-Methylsulfonyloxy-4-(4-(4-phenylbenzoylamino)butyl)-1,2,3,4,4a,5,6,10b-octahydrobenzo[f]quinoline hydrochloride Methanesulfonyl chloride (0.04 ml, 0.5 mmol) was added to a stirred solution of trans-7-hydroxy-4-(4-(4-phenylbenzoylamino)butyl)-1,2,3,4,4a,5,6,10b-octahydrobenzo[f]quinoline(E3, 200 mg, 0.4 mmol) and triethylamine (0.07 ml, 0.5 mmol) in dichloromethane (5 ml) at room temperature. The mixture was stirred for 12 h and then poured onto saturated aqueous K$_2$CO$_3$ (10 ml) and extracted onto dichloromethane (3×10 ml). The combined extracts were washed with brine, dried (Na$_2$SO$_4$) and evaporated in vacuo to give an off-white solid. Chromatography on silica using 50–100% ethyl acetate /pentane as elution gradient, afforded the free base of the title compound (200 mg, 94%). The free base was treated with 1M ethereal HCl in dichloromethane to afford after evaporation the title compound as a colourless solid.

Mass Spectrum (API+): 533 (MH+.100%) $C_{31}H_{36}N_2O_4S$ requires 532

$^1$H NMR (CDCl$_3$) δ: 1.3–2.7 (9H, m), 2.7–3.6 (1OH, m), 3.46 (3H, s), 7.28–7.50 (7H, m), 7.74–7.77 (4H, m), 7.97 (2H, d, J=10 Hz), 8.65 (1H, m), 10.85 (1H, br s).

The following compounds were prepared in a similar manner to example 5

(a) (±)-trans-2,3,3a,4,5,9b-Hexahydro-6-methylsulfonyloxy-3-(4-(4-phenylbenzoylamino)butyl)-1H-benz[e]indole (free base)

Mass spectrum (API+): Found 519 (MH+). $C_{30}H_{34}N_2O_4S$ requires 518.

$^1$H NMR (CDCl$_3$) δ: 1.54–1.88 (6H, m), 2.16 (3H, m), 2.42 (2H, m), 2.73–2.99 (3H, m), 3.08 (1H, d, J=9 Hz), 3.19 (3H, s), 3.48 (3H, m), 6.77 (1H, m), 7.01 (1H, m), 7.15 (2H, m), 7.43 (3H, m), 7.57 (2H, d, J=9 Hz), 7.64 (2H, d, J=9 Hz), 7.84 (2H, d, J=9 Hz).

(b) (4aS, 10bS)-trans-7-Methylsulfonyloxy-4-(4-(4-phenylbenzoylamino)butyl)-1,2,3,4,4a,5,6,10b-octahydrobenzo[f]quinoline Mass spectrum (API+): Found 533 (MH+). $C_{31}H_{36}N_2O_4S$ requires 532.

$^1$H NMR (CDCl$_3$) δ: 1.25 (1H, m), 1.55 (1H, m), 1.56–1.89 (6H, m), 2.06–2.87 (3H, m), 2.88–2.67 (3H, m), 2.69–3.13 (4H, m), 3.17 (3H, s), 3.52 (2H, m), 6.60 (1H, m), 7.09–7.27 (3H, m), 7.44 (3H, m), 7.62 (4H, m), 7.85 (2H, d, J=9 Hz).

EXAMPLE 6 cis-7-Methylsulfonyloxy-4-(4-(4-phenylbenzoylamino) butyl)-1,2,3,4,4a,5,6,10b-octahydrobenzo[f]quinoline Hydrochloride Methanesulfonyl chloride (0.04 ml, 0.5 mmol) was added to stirred solution of cis-7-hydroxy-4-(4-(4-phenylbenzoylamino)butyl)-1,2,3,4,4a,5,6,10b-octahydrobenzo[f]quinoline (E4, 200 mg, 0.4 mmol) and triethylamine (0.07 ml, 0.5 mmol) in dichloromethane (5 ml) at room temperature. The mixture was stirred for 2 h and then poured onto saturated aqueous K$_2$CO$_3$ (10 ml) and extracted into dichloromethane (3×10 ml). The combined organic extracts were washed with brine, dried (Na$_2$SO$_4$) and evaporated in vacuo to give a solid which was chromatographed on silica using 50–100% ethyl acetate/pentane as elution gradient to give the free base of the title compound (156 mg, 73%). The free base was treated with 1M ethereal HCl in dichloromethane to afford after evaporation the title compound as a colourless solid.

Mass spectrum (API+): 533 (MH+ 100%) $C_{31}H_{36}N_2O_4S$ requires 532.

$^1$H NMR (CDCl$_3$) δ: 1.55–2.16 (11H, m), 2.7–3.65 (13H, m), 7.17–7.52 (7H,m), 7.70–7,78 (3H, m), 7.96 (2H, m), 10.85 (1H, m).

EXAMPLE 7 trans-4-(4-Phenylbenzoylamino)butyl)-1,2,3,4,4a,5,6,10b-octahydrobenzo[f]quinoline Sodium triacetoxyborohydride (340 mg, 1.6 mmol) was added to a stirred mixture of trans-1,2,3,4,4a,5,6,10b-octahydrobenzo[f]quinoline (D8a, 200 mg, 1 mmol), 4-(4-phenylbenzoylamino)butyraldehyde (286 mg, 01.1 mmol) and acetic acid (1 drop) in 1,2-dichloroethane (10 ml) at room temperature. After stirring for 16 h, dichloromethane (20 ml) was added and the mixture was then washed with saturated aqueous K$_2$CO$_3$ (2×25 ml) and brine (25 ml). Drying (Na$_2$SO$_4$) and evaporation in vacuo afforded an oil which was purified by preparative TLC on Kieselgel using 10% methanol-ethyl acetate as eluent to give the title compound as a colourless solid (200 mg, 46%).

Mass Spectrum: found M+ 438.2678; $C_{30}H_{34}N_2O$ requires 438.2671

$^1$H NMR (CDCl$_3$) δ: 1.25 (1H, m), 1.58 (5H, m), 1.8 (2H, m), 2.19 (3H, m), 2.48 (2H, m), 2.64 (1H, m), 2.84 (2H, m), 3.09 (1H, m), 3.51 (2H, m), 6.68 (1H, m), 7.10 (3H, m), 7.25 (1H, d), 7.35 (1H, m), 7.45 (2H, m), 7.60 (4H, m), 7.80 (2H, d).

EXAMPLE 8 cis-4-(4-(4-Phenylbenzoylamino)butyl)-1,2,3,4,4a,5,6,10b-octahydrobenzo[f]quinoline Sodium triacetoxyborohydride (170 mg, 0.8 mmol) was added to a stirred mixture of cis-1,2,3,4,4a,5,6,10b-octahydrobenzo[f]quinoline (D8b, 100 mg, 0.5 mmol), 4-(4-phenylbenzoylamino)butyraldehyde (143, 0.54 mmol) and acetic acid (1 drop) in 1,2-dichloroethane (8 ml) at room temperature. After stirring for 16 h, dichloromethane (10 ml) was added and the mixture was then washed with saturated aqueous K$_2$CO$_3$ (2×20 ml) and brine (20 ml). Drying (Na$_2$SO$_4$) and evaporation in vacuo afforded an oil which was purified by preparative TLC on Kieselgel using 10% methanol-ethyl acetate as eluent to give the title compound as a gum (150 mg, 68%). Mass spectrum: found M+ 438.2679; $C_{30H34}N_2O$ requires 438.2671.

$^1$H NMR (CDCl$_3$) δ: 1.71 (9H, m), 1.96 (1H, m), 2.47 (1H, m), 2.68 (3H, m), 2.76 (1H, m), 2.94 (2H, m), 3.2 (1H, m), 3.51 (2H, m), 6.75 (1H, br s), 7.05 (4H, m), 7.35 (1H, m), 7.45 (2H, m), 7.60 (4H, m), 7.85 (2H, d).

EXAMPLE 9 cis-2,3,3a,4,9,9a-Hexahydro-1-(4-(4-phenylbenzoylamino) butyl)-1H-benz[f]indole Hydrochloride A mixture of cis-2,3,3a,4,9,9a-hexahydro-1H-benz[f] indole (D16, 0.54 g, 3.12 mmol), 4-(4-phenylbenzoylamino) butyraldehyde (0.83 g, 3.12 mmol) and sodium triacetoxyborohydride (0.97 g, 4.7 mmol) in dichloroethane (120 ml) was stirred at room temperature for 18 h. Resulting mixture was partitioned between saturated aqueous NaHCO$_3$ (200 ml) and dichloromethane (3×50 ml). The combined extracts were dried (Na$_2$SO$_4$) and evaporated in vacuo to give an oil (1.77 g). Chromatography on silica eluting with 50–100%-dichloromethane-hexane and then 0–6% methanol-dichloromethane gave the free base of the title compound as a colourless solid (0.55 g, 42%). The free base was treated with 1M ethereal HCl (2.6 ml, 2.6 mmol) in dichloromethane to afford after evaporation the title compound as a colourless solid (0.53 g, 89%).

Mass spectrum (API+): 425 (MH+). $C_{29}H_{32}N_2O$ requires 424.

$^1$H NMR (DMSO-d$_6$) δ: 1.66 (3H, m), 1.83 (2H, m), 2.30 (1H, m), 2.60 (2H, m), 2.85 (1H, m), 3.07 (3H, m), 3.24 (1H, m), 3.36 (2H, m), 3.45 (1H, m), 3.58 (1H, m), 3.68 (1H, m), 7.19 (4H, s), 7,42 (1H, m), 7.50 (2H, t, J=8 Hz), 7.74 (4H, m), 7.98 (2H, d, J=9 Hz), 8.64 (1H, m), 10.24 and 10.70 (1H, 2×br s). Elemental Analysis: found: C, 74.26; H, 7.07; N, 5.91%; $C_{29}H_{32}N_2O$. HCl. 0.5H$_2$O requires C, 74.10; H, 7.29; N, 5.96%.

EXAMPLE 10 cis-2,3,3a,4,9,9a-Hexahydro-5-methoxy-1-(4-(4-phenylbenzoylamino)butyl)-1H-benz[f]indole Hydrochloride A mixture of cis-2,3,3a,4,9,9a-hexahydro-5-methoxy-1H-benz[f]indole (D17, 0.08 g, 0.39 mmol), 4-(4-phenylbenzoylamino)butyraldehyde (0.11 g, 0.40 mmol), and sodium triacetoxyborohydride (0.13 g, 0.61 mmol) in dichioroethane (20 ml), was stirred at room temperature for 18 h. Resulting mixture was partitioned between saturated aqueous NaHCO$_3$ (20 ml) and dichloromethane (3×10 ml). The combined extracts were dried (Na$_2$SO$_4$) and evaporated in vacuo to give an oil. Chromatography on silica using 0–4% methanol-dichloromethane gradient elution gave the free base of the title compound as a colourless solid (0.07 g, 38%). The free base was treated with 1M ethereal HCl (0.31 ml, 0.3 mmol) in dry dichloromethane to afford after evaporation the title compound.

Mass spectrum (EI$^+$): 454.2602 (M$^+$); C$_{30}$H$_{34}$N$_2$O$_2$ requires 454.2620.

$^1$H NMR (DMSO-d$_6$) δ: 1.63 (3H, m), 1.79 (2H, m), 2.31 (2H, m), 2.52 (2H, m), 3.06 (4H, m), 3.21 (1H, m), 3.35 (2H, m), 3.41 (1H, m), 3.57 (1H, m), 3.65 (1H, m), 3.77 (3H, s), 6.85 (2H, m), 7.14 (1H, t, J=8 Hz), 7.41 (1H, m), 7.48 (2H, t, J=7 Hz), 7.74 (4H, m), 7.97 (2H, d, J=8 Hz), 8.63 (1H, m), 10.13 and 10.70 (1H, 2×br s).

What is claimed is:

1. A compound of formula (I):

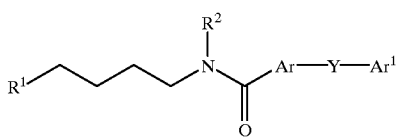

Formula (I)

wherein R$^1$ represents a group of formula (A) or (B):

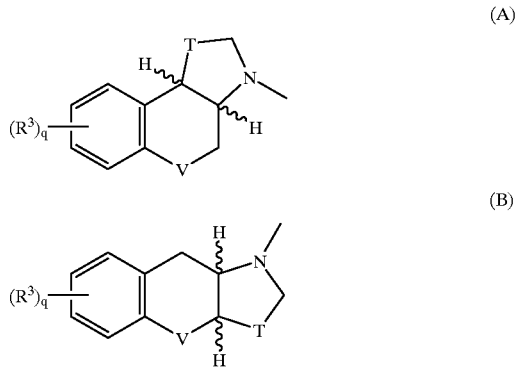

R$^2$ represents a hydrogen atom or a C$_{1-4}$alkyl group;

R$^3$ represents a substituent selected from: a hydrogen or halogen atom, a hydroxy, cyano, trifluoromethyl, trifluoromethoxy, trifluoromethanesulfonyloxy, C$_{1-4}$alkyl, C$_{1-4}$alkoxy, arylC$_{1-4}$alkoxy, C$_{1-4}$alkylthio, C$_{1-4}$alkoxyC$_{1-4}$alkyl, C$_{3-6}$cycloalkylC$_{1-4}$alkoxy, C$_{1-4}$alkanoyl, C$_{1-4}$alkylsulphonyl, C$_{1-4}$alkylsulphonyloxy, C$_{1-4}$alkylsulphonylC$_{1-4}$alkyl, arylsulphonyl, arylsulphonyloxy or arylsulphonylC$_{1-4}$alkyl group wherein aryl is selected from an optionally substituted phenyl or an optionally substituted 5- or 6-membered heterocyclic ring, a group R$^{3'}$OCO(CH$_2$)$_p$, R$^{3'}$R$^4$NCO(CH$_2$)$_p$ or R$^{3'}$R$^4$NSO$_2$(CH$_2$)$_p$ where each of R$^{3'}$ and R$^4$ independently represents a hydrogen atom or a C$_{1-4}$alkyl group and p represents zero or an integer from 1 to 4, or a group Ar$^2$—Z, wherein Ar$^2$ represents an optionally substituted phenyl ring or an optionally substituted 5-or 6-membered aromatic heterocyclic ring and Z represents a bond, O, S, or CH$_2$;

q is 1 or 2;

T represents CH$_2$, CH$_2$CH$_2$ or OCH$_2$;

V represents CH$_2$, O or a bond;

Ar and Ar$^1$ each independently represent an optionally substituted phenyl ring; and Y represents a bond, —NHCO—, —CONH—, —CH$_2$—, or —(CH$_2$)$_m$Y$^1$(CH$_2$)$_n$—, wherein Y$^1$ represents O, S, SO$_2$, or CO and m and n each represent zero or 1 such that the sum of m+n is zero or 1; or a salt thereof.

2. A compound according to claim 1 wherein q represents 1.

3. A compound according to claim 2 wherein Y represents a bond.

4. A compound according to claim 3 wherein Ar and Ar$^1$ both represent unsubstituted phenyl.

5. A compound of formula (I) which is:

trans-7-methoxy-4-(4-(4-phenylbenzoylamino)butyl)-1,2,3,4,4a,5,6,10b-octahydrobenzo[f]quinoline;

cis-7-methoxy-4-(4-(4-phenylbenzoylamino)butyl)-1,2,3,4,4a,5,6,10b-octahydrobenzo[f]quinoline;

trans-7-hydroxy-4-(4-(4-phenylbenzoylamino)butyl)-1,2,3,4,4a,5,6,10b-octahydrobenzo[f]quinoline;

cis-7-hydroxy-4-(4-(4-phenylbenzoylamino)butyl)-1,2,3,4,4a,5,6,10b-octahydrobenzo[f]quinoline;

trans-7-methylsulfonyloxy-4-(4-(4-phenylbenzoylamino)butyl)-1,2,3,4,4a,5,6,10b-octahydrobenzo[f]quinoline;

cis-7-methylsulfonyloxy-4-(4-(4-phenylbenzoylamino)butyl)-1,2,3,4,4a,5,6,10b-octahydrobenzo[f]quinoline;

trans-4-(4-(4-phenylbenzoylamino)butyl)-1,2,3,4,4a,5,6,10b-octahydrobenzo[f]quinoline;

cis-4-(4-(4-phenylbenzoylamino)butyl)-1,2,3,4,4a,5,6,10b-octahydrobenzo[f]quinoline;

cis-2,3,3a,4,9,9a-hexahydro-1-(4-(4-phenylbenzoylamino)butyl)-1H-benz[f]indole;

cis-2,3,3a,4,9,9a-hexahydro-5-methoxy-1-(4-(4-phenylbenzoylamino)butyl)-1H-benz[f]indole;

trans-8-methoxy-4-(4-(4-phenylbenzoylamino)butyl)-1,2,3,4,4a,5,6,10b-octahydrobenzo[f]quinoline;

trans-2,3,3a,4,5,9b-hexahydro-3-(4-(4-phenylbenzoylamino)butyl)-1H-benz[e]indole;

trans-2,3,3a,4,5,9b-hexahydro-6-methoxy-3-(4-(4-phenylbenzoylamino)butyl-1H-benz[e]indole;

(4aS, 10bS)-trans-7-methoxy-4-(4-(4-phenylbenzoylamino)butyl)-1,2,3,4,4a,5,6,10b-octahydrobenzo[f]quinoline;

trans-8-hydroxy-4-(4-(4-phenylbenzoylamino)butyl)-1,2,3,4,4a,5,6,10b-octahydrobenzo[f]quinoline;

trans-2,3,3a,4,5,9b-hexahydro-6-hydroxy-3-(4-(4-phenylbenzoylamino)butyl)-1H-benz[e]indole;

(4aS, 10bS)-trans-7-hydroxy-4-(4-(4-phenylbenzoylamino)butyl)-1,2,3,4,4a,5,6,10b-octahydrobenzo[f]quinoline;

trans-2,3,3a,4,5,9b-hexahydro-6-methylsulfoxyloxy-3-(4-(4-phenylbenzoylamino)butyl)-1H-benz[e]indole;

(4aS, 10bS)-trans-7-methylsulfonyloxy-4-($^4$-($^4$-phenylbenzoylamino)butyl)-1,2,3,4,4a,5,6,10b-octahydrobenzo[f]quinoline;

or a salt thereof.

6. A process for preparing a compound of formula (I) as defined in claim 1 which process comprises:

(a) reacting a compound of formula (II):

$$R^1H \qquad \text{Formula (II)}$$

wherein $R^1$ is as defined in claim 1;
with a compound of formula (III):

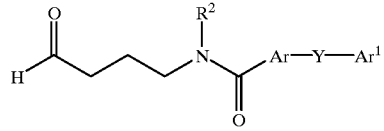

Formula (III)

wherein $R^2$, Y, Ar, and $Ar^1$ are as defined in claim 1; or (b) reaction of a compound of formula (IV):

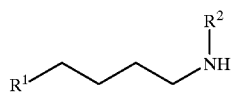

Formula (IV)

wherein $R^1$ and $R^2$ are as defined in claim 1;
with a compound of formula (V):

$$Ar^1\text{—}Y\text{—}ArCOX \qquad \text{Formula (V)}$$

wherein Y, Ar and $Ar^1$ are as defined in claim 1 and X is a halogen atom or the residue of an activated ester; or (c) to prepare a compound of formula (I) where Y is a bond, reaction of a compound of formula (VI):

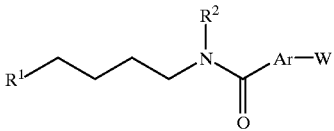

Formula (VI)

wherein $R^1$, $R^2$ and Ar are as defined in claim 1, and W is a halogen atom or a trifluoromethylsulphonyloxy group, or W is a group M selected from a boron derivative or a metal function;

with a compound:

$$Ar^1\text{—}W^1$$

wherein $W^1$ is a halogen atom or a trifluoromethylsulphonyloxy group when W is a group M, or $W^1$ is a group M when W is a halogen atom or a trifluoromethylsulphonyloxy group; and optionally thereafter forming a salt of formula (I).

7. A pharmeceutical composition comprising a compound of formula (I) as claimed in claim 1 or a physiologically acceptable salt thereof and a pharmaceutically acceptable carrier therefor.

8. A method of treating a condition which requires antagonism of a dopamine receptor which comprises administering to a subject in need thereof an effective amount of a compound of formula (I) as claimed in claim 1 or a pharmaceutically acceptable salt thereof.

9. A method according to claim 8 wherein the condition is a psychotic condition.

* * * * *